(12) United States Patent
Lim et al.

(10) Patent No.: US 9,423,402 B2
(45) Date of Patent: Aug. 23, 2016

(54) GM1 GANGLIOSIDE TO ANNEXIN V MICROPARTICLE POLYPEPTIDE RATIO FOR BIOLOGICAL MONITORING

(71) Applicants: Agency for Science, Technology and Research, Singapore (SG); Singapore Health Services Pte Ltd., Singapore (SG)

(72) Inventors: Sai Kiang Lim, Singapore (SG); Kok Hian Tan, Singapore (SG)

(73) Assignees: SINGAPORE HEALTH SERVICES PTE. LTD., Singapore (SG); **AGENCY FOR SCIENCE, TECHNOLOGY AND RESEARCH (A*STAR)**, Singapore (SG)

( * ) Notice: Subject to any disclaimer, the term of this patent is extended or adjusted under 35 U.S.C. 154(b) by 0 days.

(21) Appl. No.: 14/361,500

(22) PCT Filed: Nov. 30, 2012

(86) PCT No.: PCT/SG2012/000451
§ 371 (c)(1),
(2) Date: May 29, 2014

(87) PCT Pub. No.: WO2013/081554
PCT Pub. Date: Jun. 6, 2013

(65) Prior Publication Data
US 2014/0323595 A1    Oct. 30, 2014

(30) Foreign Application Priority Data

Nov. 30, 2011 (SG) .................................. 201108886-1
Apr. 18, 2012 (SG) .................................. 201202838-7

(51) Int. Cl.
*C12Q 1/00* (2006.01)
*G01N 33/68* (2006.01)
*G01N 33/50* (2006.01)

(52) U.S. Cl.
CPC ........ *G01N 33/6872* (2013.01); *G01N 33/5091* (2013.01); *G01N 33/689* (2013.01); *G01N 33/6893* (2013.01); *G01N 2405/10* (2013.01); *G01N 2800/32* (2013.01); *G01N 2800/368* (2013.01)

(58) Field of Classification Search
CPC .................................................. G01N 33/6872
See application file for complete search history.

(56) References Cited

U.S. PATENT DOCUMENTS

| 8,962,318 B2 | 2/2015 | Lim et al. |
|---|---|---|
| 9,029,318 B2 | 5/2015 | Zlotkin et al. |
| 2003/0175831 A1 | 9/2003 | Canton et al. |
| 2008/0199849 A1 | 8/2008 | Lim et al. |
| 2009/0311715 A1 | 12/2009 | Owen et al. |

FOREIGN PATENT DOCUMENTS

| WO | 2005/114192 A1 | 12/2005 |
|---|---|---|
| WO | 2006/027545 A2 | 3/2006 |
| WO | 2007/027156 A1 | 3/2007 |
| WO | 2007/027157 A1 | 3/2007 |
| WO | 2008/020815 A1 | 3/2008 |
| WO | 2009/105044 A1 | 8/2009 |
| WO | 2011/127219 A1 | 10/2011 |

OTHER PUBLICATIONS

Johnson et al., "Temperature-dependent phase behavior and protein partitioning in giant plasma membrance vesicles", Biochim Biophys Acta, 1798(7):142-1435 (2010).
Mattei et al., "Paracrine diffusion of PrP(C) and propagation of prion infectivity by plasma membrane-derived microvesicles", PLOS one 4(4):e5057 (2009).
Arnold et al., "A quantitative electrophoretic migration shift assay for analyzing the specific binding of proteins to lipid ligands in vesicles or micelles", Biochimica et Biophysica Acta 1233: 198-201 (1995).
Tan et al., "Plasma biomarker discovery in preeclampsia using a novel differntial isolation technology for circulating extracellular vesicles", Am J Obstet Gynecol, 211: 380.e1-13 (2014).
Carton et al., "label-Free Detection of Clustering of Membrane-Bound Proteins", Anal Chem, 82: 9275-9281 (2010).

*Primary Examiner* — Albert Navarro
(74) *Attorney, Agent, or Firm* — Nixon Peabody LLP; Mark J. FitzGerald

(57) ABSTRACT

We describe a method of monitoring the state of a cell, tissue, organ or organism. The method comprises establishing, for a sample of microparticles from the cell, tissue, organ or organism, a ratio. The ratio is of a selected polypeptide in microparticles which comprise GM1 gangliosides, preferably which bind to Cholera Toxin B (CTB) ("GM1 ganglioside microparticle polypeptide") to the selected polypeptide in microparticles which comprise exposed phosphotidylserine, preferably which bind to Annexin V ("Annexin V microparticle polypeptide"). The GM1 ganglioside microparticle polypeptide to Annexin V microparticle polypeptide ratio so established may be indicative of the state of the cell, tissue, organ or organism.

8 Claims, 11 Drawing Sheets

A.

GM1 GANGLIOSIDE TO ANNEXIN V MICROPARTICLE POLYPEPTIDE RATIO FOR BIOLOGICAL MONITORING

CROSS REFERENCE TO RELATED APPLICATIONS

This application is a 35 U.S.C. 371 National Phase Entry Application of International Application No. PCT/SG2012/000451 filed Nov. 30, 2012, which designates the U.S., and which claims benefit of Singapore Application No. 201108886-1, filed on Nov. 30, 2011 and Singapore Application No. 201202838-7 filed on Apr. 18, 2012 the contents of which are incorporated herein by reference in their entireties.

FIELD

The present invention relates to the fields of medicine, cell biology, molecular biology and genetics. This invention relates to the field of medicine.

In particular, it relates to methods of monitoring the physiological or pathological state of a cell, tissue, organ or organism. The invention also relates to the diagnosis and treatment of diseases such as cancer.

Reference is made to U.S. Patent Application No. 60/713,992, Ser. Nos. 12/065,549, 12/065,551, 60/878,222, Ser. No. 12/377,398, 61/066,671, 61/227,865 and 61/257,121. Reference is also made to International Patent Application Numbers PCT/GB2005/003206, PCT/SG2006/000233, PCT/SG2006/000232, PCT/SG2007/000257 and PCT/SG2009/000062.

The foregoing applications, and each document cited or referenced in each of the present and foregoing applications, including during the prosecution of each of the foregoing applications ('application and article cited documents'), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

BACKGROUND

It is well established that microparticles are secreted by different cell types and could be different depending on the cell type and the pathophysiological conditions of the cell or cellular microenvironment such as Alzheimer disease, TB infection, HIV infection, cancer, hypoxia, irradiation, oxidative stress, shearing stress, and exposure activated complement complexes. Microparticles are membrane vesicles. To date, there are several types of microparticles that include exosomes, ectosomes, apoptotic bodies[2]. These microparticles contain both proteins and RNAs. Many of these microparticles have been shown to have biological activities that enhance either biological activities or pathogenesis.

Bodily fluids such as urine, blood, tears, saliva, bronchoaveolar fluid, tumoral effusions, epididymal fluid, amniotic fluid and milk contain many membrane vesicles. As the shedding, type and biological activity of microparticles is dependent on the cell type, their physiological state and their cellular microenvironment, these microparticles are potentially a good source of diagnostic or prognostic markers. Depletion of these microparticles could also be potentially therapeutic. However, the identity and origin of many of these microparticles in bodily fluids are unknown and presumably, are also highly heterogenous.

Therefore, there is a need in the art for tools that can rapidly enrich for these microparticles and that will improve the predictability and robustness of lipid microparticle-based biomarkers or therapeutic applications.

SUMMARY

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

An aliquot from the input serum, flow through and washes was resolved by SDS/PAGE and the gel was stained with silver (upper panel) or electroblotted on nitrocellulose for western blot hybridization using an anti-CD9 antibody (lower panel).

Figure 2:
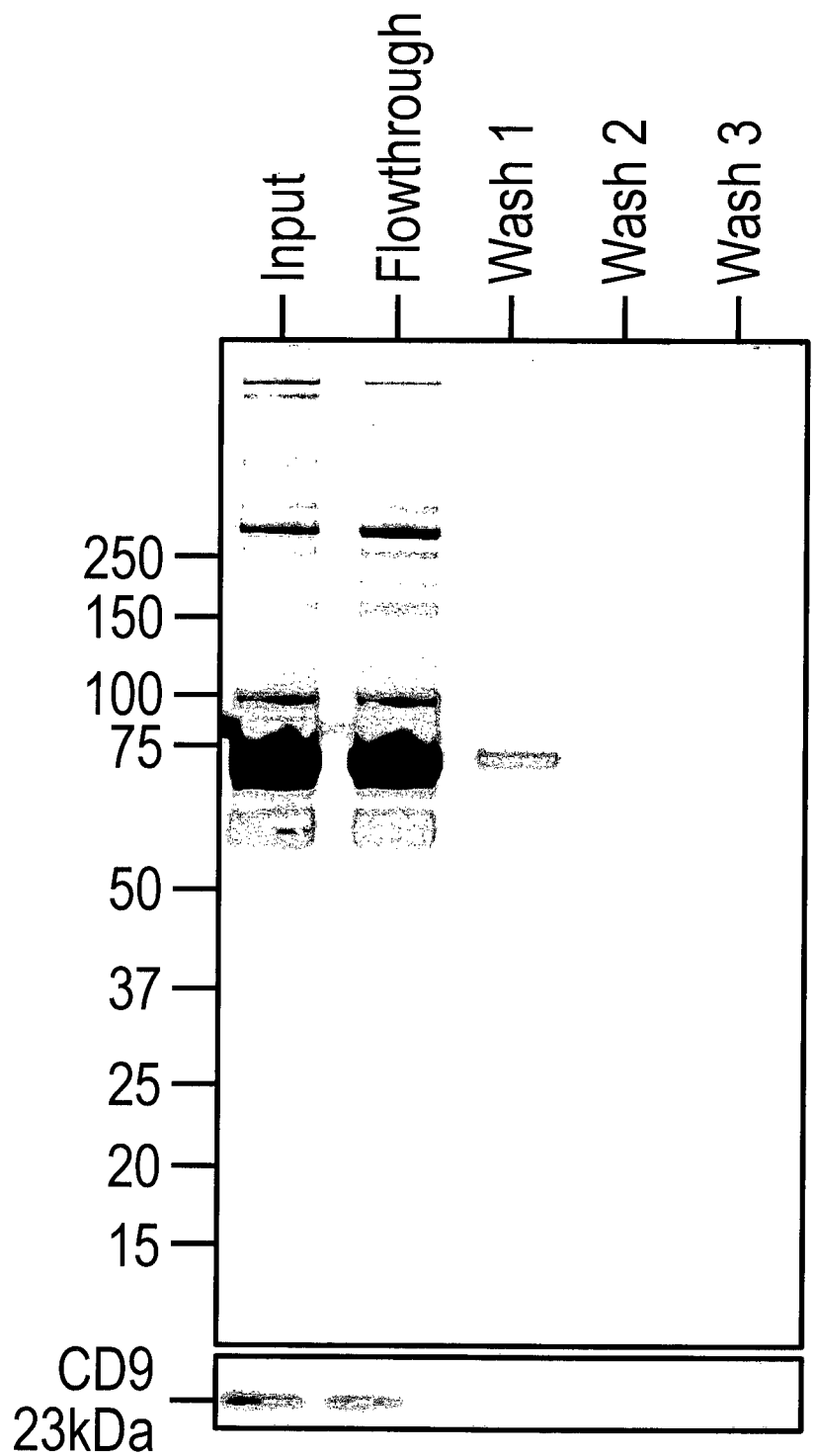

FIG. 2 is a diagram showing CTB affinity chromatography. The flow through and wash 1 fractions after size exclusion chromatography of the serum were pooled and tested for the presence of GM1 ganglioside by CTB affinity chromatography.

The fractions were incubated with biotinylated CTB and then strepavidin-coupled to magnetic beads before being washed three times with PBS. An aliquot from the input serum, flow through (or unbound fraction) and washes was resolved by SDS/PAGE and the gel was stained with silver (upper panel) or electroblotted on nitrocellulose for western blot hybridization using an anti-CD9 antibody (lower panel).

Figure 3:
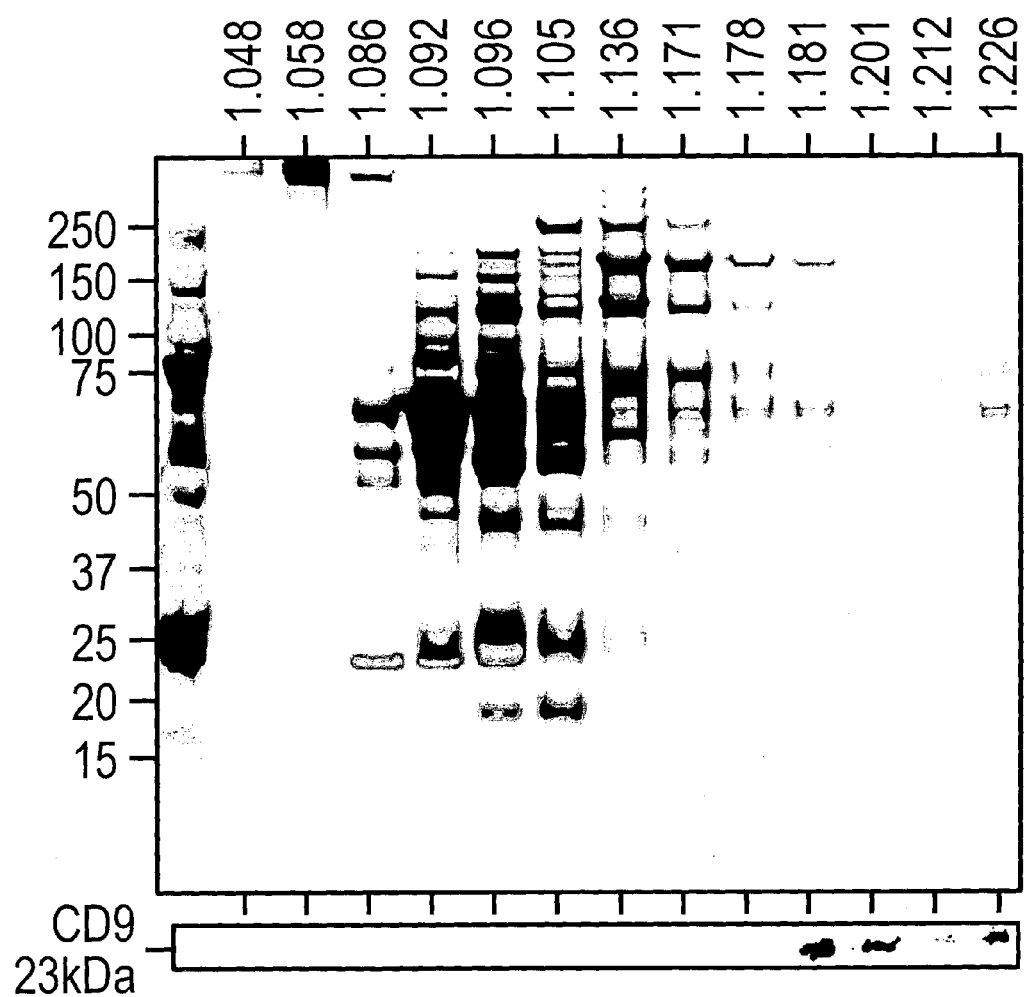

FIG. 3 is a diagram showing sedimentation of CD9+ microparticles in sucrose density gradient. Serum was sedimented in a sucrose density gradient from 22.8% to 60% w/v. After ultracentrifugation, the gradient was fractionated in equal volumes. Each fraction was weighed and the density calculated.

An aliquot from each fraction denoted by the density (g/ml) at the top of the upper panel was resolved by SDS/PAGE and the gel was stained with silver (upper panel) or electroblotted on nitrocellulose for western blot hybridization using an anti-CD9 antibody (lower panel).

Figure 4:
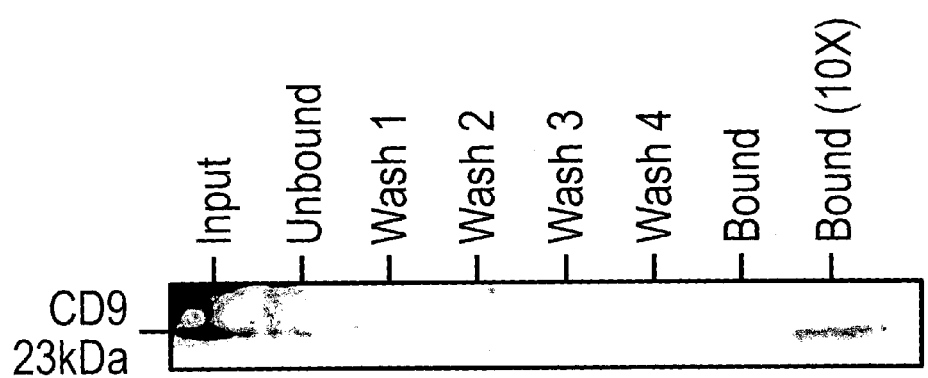

FIG. 4 is a diagram showing Annexin V affinity chromatography. Serum was incubated with biotinylated annexin V and then strepavidin-coupled to magnetic beads before being washed three times with PBS.

An equivalent aliquot from the input serum, flow through (or unbound fraction) and washes was resolved by SDS/PAGE and electroblotted on nitrocellulose for western blot hybridization using an anti-CD9 antibody. The Bound (10×) aliquot was 10 times more that that used in each of the other lanes.

Figure 5:
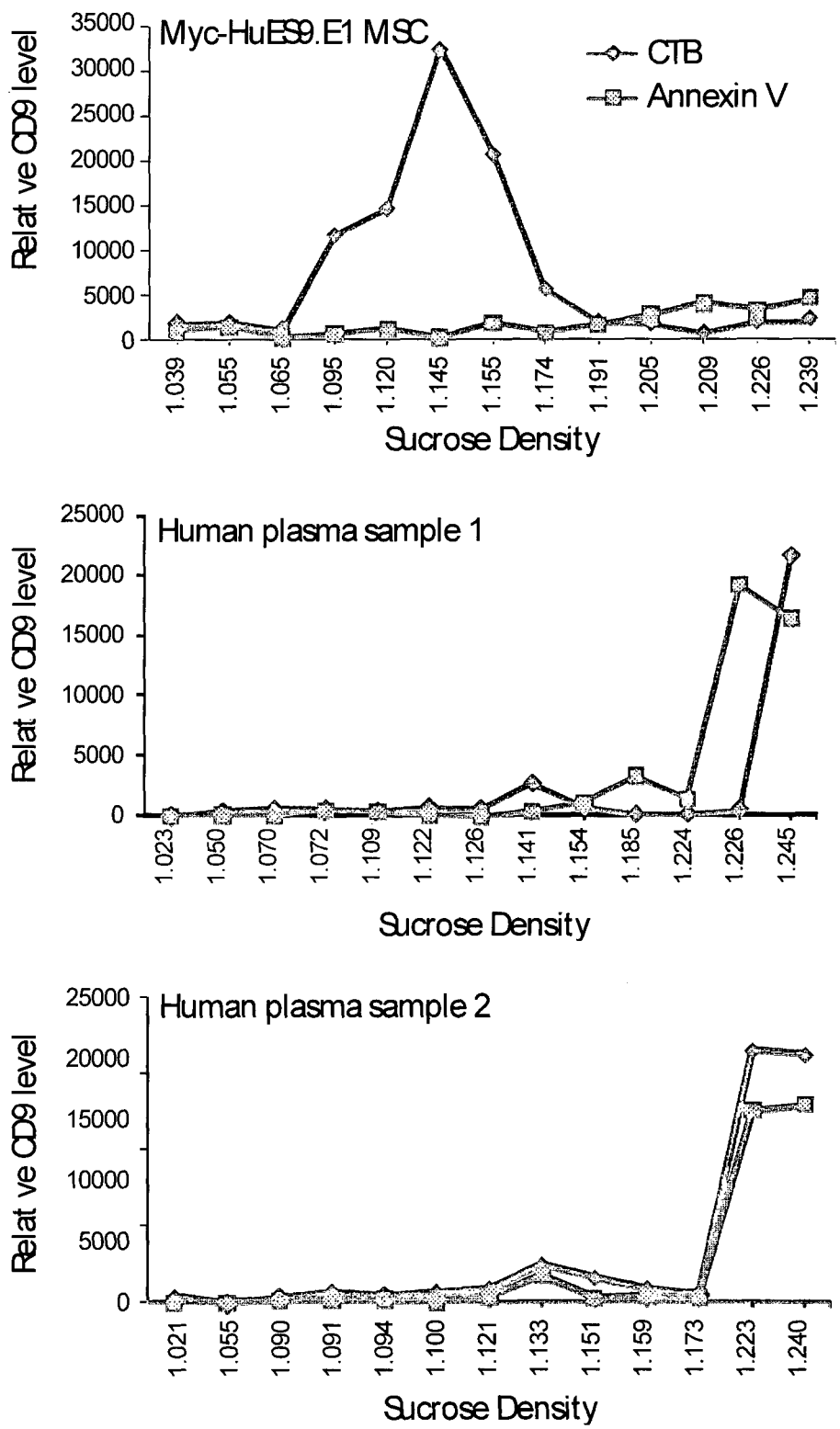

FIG. 5. Culture medium conditioned by Myc-transformed ES-derived MSC line (Myc-HuES9.E1) and plasma were loaded onto a sucrose density gradient. The gradient was prepared by layering 14 sucrose solutions of concentrations from 23% to 60% (w/v). After loading the samples, the gradient was ultracentrifuged for 18 h at 200,000 g, 4° C.

The gradient was removed from the top in 13 fractions. The density of each fraction was determined by weighing 100 µL of each fraction. The relative level of CD9+ annexin V-binding microvesicles and CD9+ CTB-binding microvesicles in each fraction were determined.

Figure 6A:
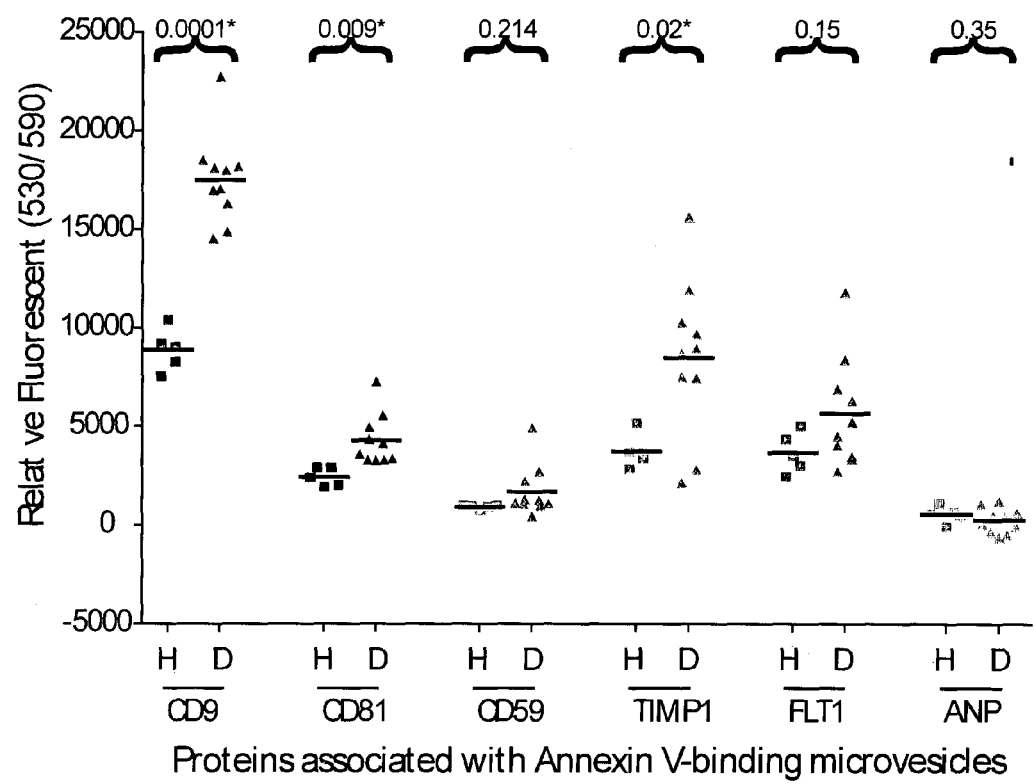
Figure 6B:
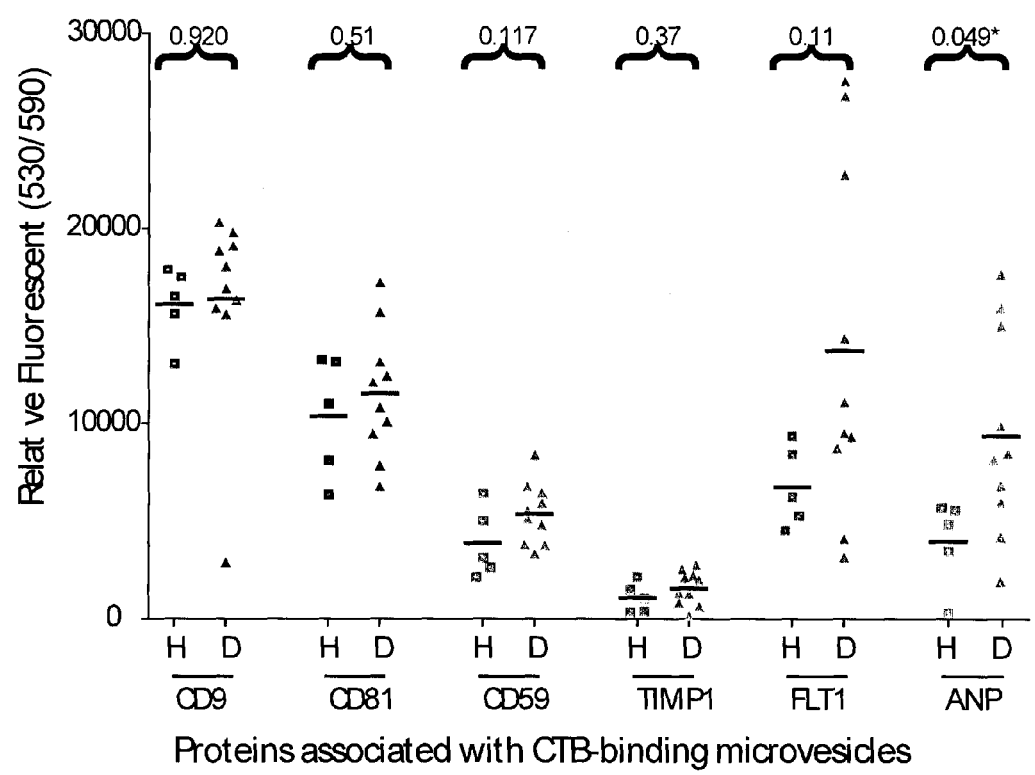

FIG. 6A and FIG. 6B. Plasma from healthy individuals (H) and cardiac patients (D) were incubated with biotinylated Annexin V (FIG. 6A) or Cholera Toxin B (FIG. 6B). Microvesicles that bind either Annexin V or Cholera Toxin B were extracted with streptavidin-conjugated magnetic beads. Proteins in these isolated microvesicles were assayed using specific antibody in an ELISA.

Figure 7:
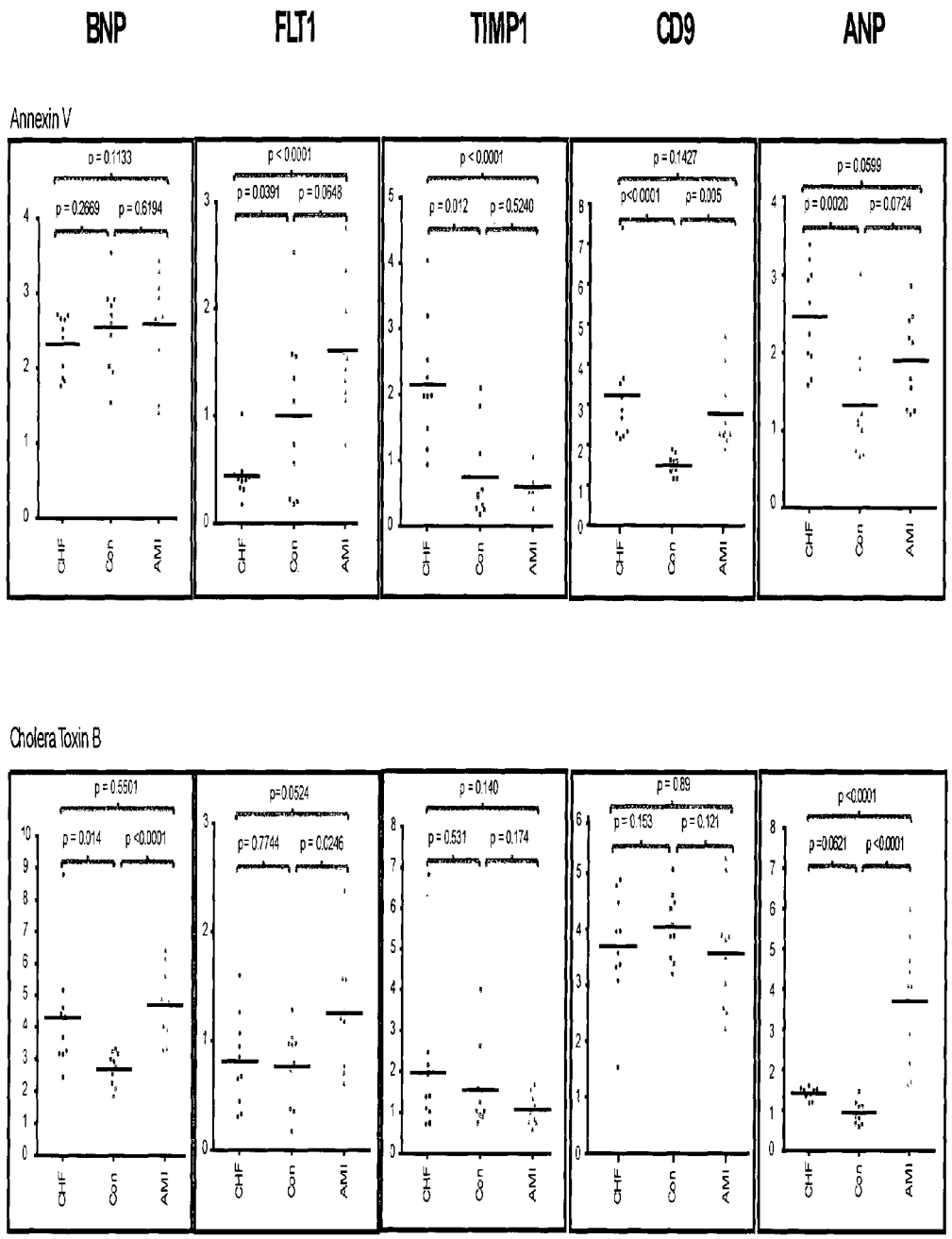

FIG. 7. For each biomarker in either microvesicle A or B, five to ten microliters of plasma from heart failure patients (CHF), healthy individuals (Con) and AMI patients (AMI) were used. The relative levels of BNP, Flt-1, TIMP-1, CD9 and ANP in either microvesicle A or B were determined by first isolating the microvesicle by affinity chromatography followed by an ELISA using antibody specific for the ligand. Flt-1 and CD9 are membrane bound proteins while BNP, TIMP-1 and ANP are luminal proteins.

The distribution of these proteins in microvesicle A or B of the different groups of patients were analysed. CHF and AMI patients had significantly higher BNP level in microvesicle B but not A, relative to Con individuals. Flt-1 in both microvesicle A and B was higher for AMI patients to Con individuals.

However, Flt-1 in microvesicle A was lower for CHF patients and that in microvesicle B was not significantly different from Con individuals. Among the microvesicles in the three patient groups, only microvesicle A-associated TIMP-1 in CHF patients was significantly different i.e. higher. CD9 in microvesicle A but not B was significantly higher in CHF and AMI patients. ANP in microvesicle A was significantly higher for CHF and AMI patients. In microvesicle B, ANP A was significantly higher only for AMI patients.

Figure 8:
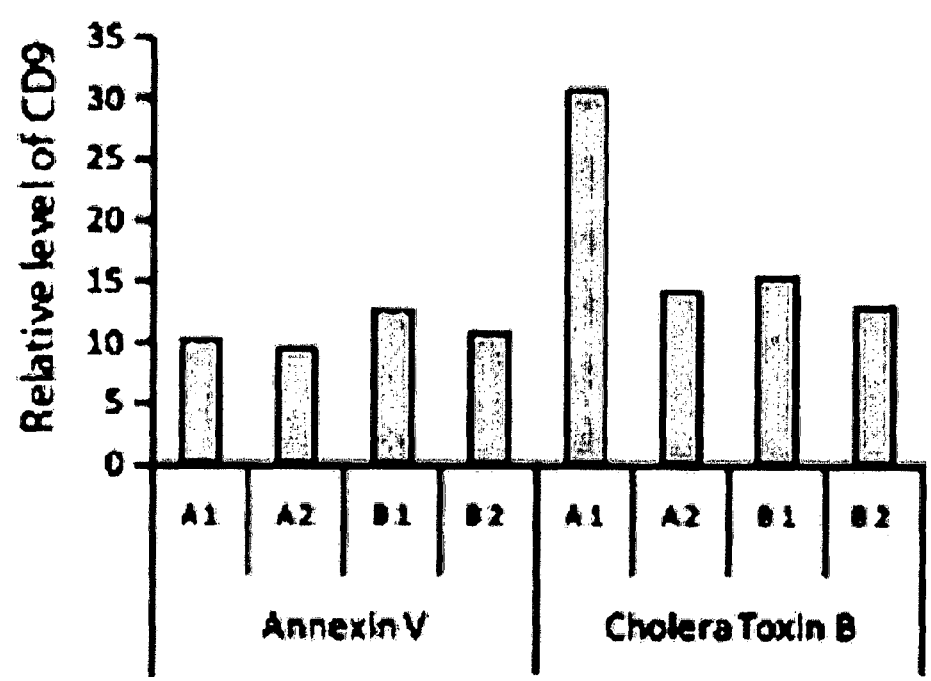

FIG. 8. Monitoring plasma CD9 of a case of food poisoning. Plasma from an individual with food poisoning was analysed as described above during and 3 weeks after the event. Two plasma samples from an healthy individual taken three weeks apart served as control. The average fluorescence in the CTB fraction and AnnV faction for patient before (A1) and three weeks after food poisoning (A2) were plotted against those of B1 and B2. B1 and B2 were the plasma samples taken three weeks apart from a healthy control.

Figure 9:
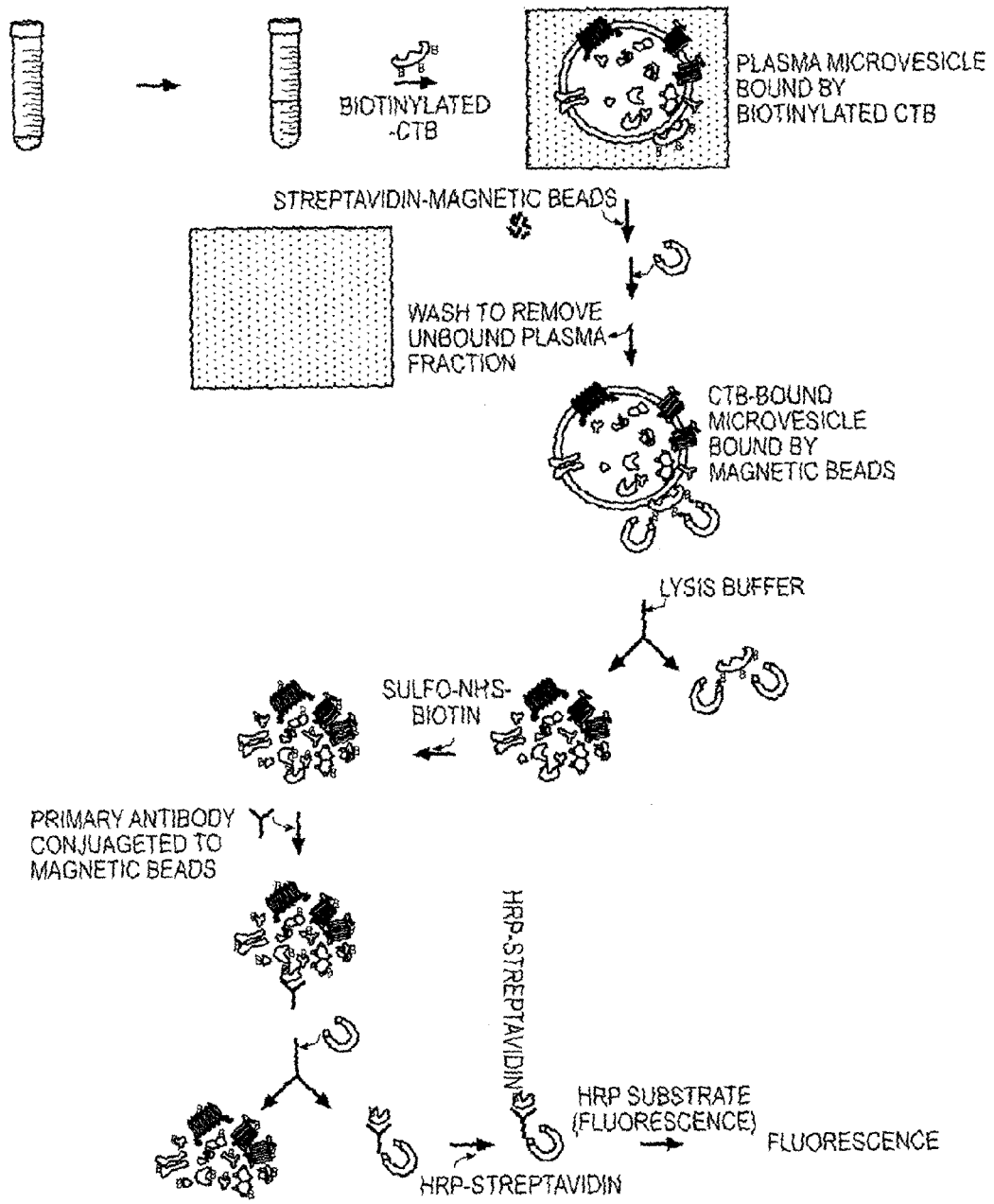

FIG. 9. Development of an Assay. Plasma is first incubated with biotinylated CTB and then with streptavidin-conjugated magnetic beads. The magnetic beads are then immobilized with a magnet and washed with PBS or a isotonic salt solution. Bound microvesicles are lysed with a generic detergent-based cell lysis buffer.

The microvesicle contents are then biotinylated by activated biotin e.g. sulfo-NHS-Biotin. To assay for a specific protein, magnetic bead conjugated antibody specific for the protein of interest is then added. The antibody-bound protein is then immobilized by magnet and washed extensively. The protein is quantified using streptavidin-conjugated HRP and a HRP colorimetric or fluorimetric substrate.

Figure 10:
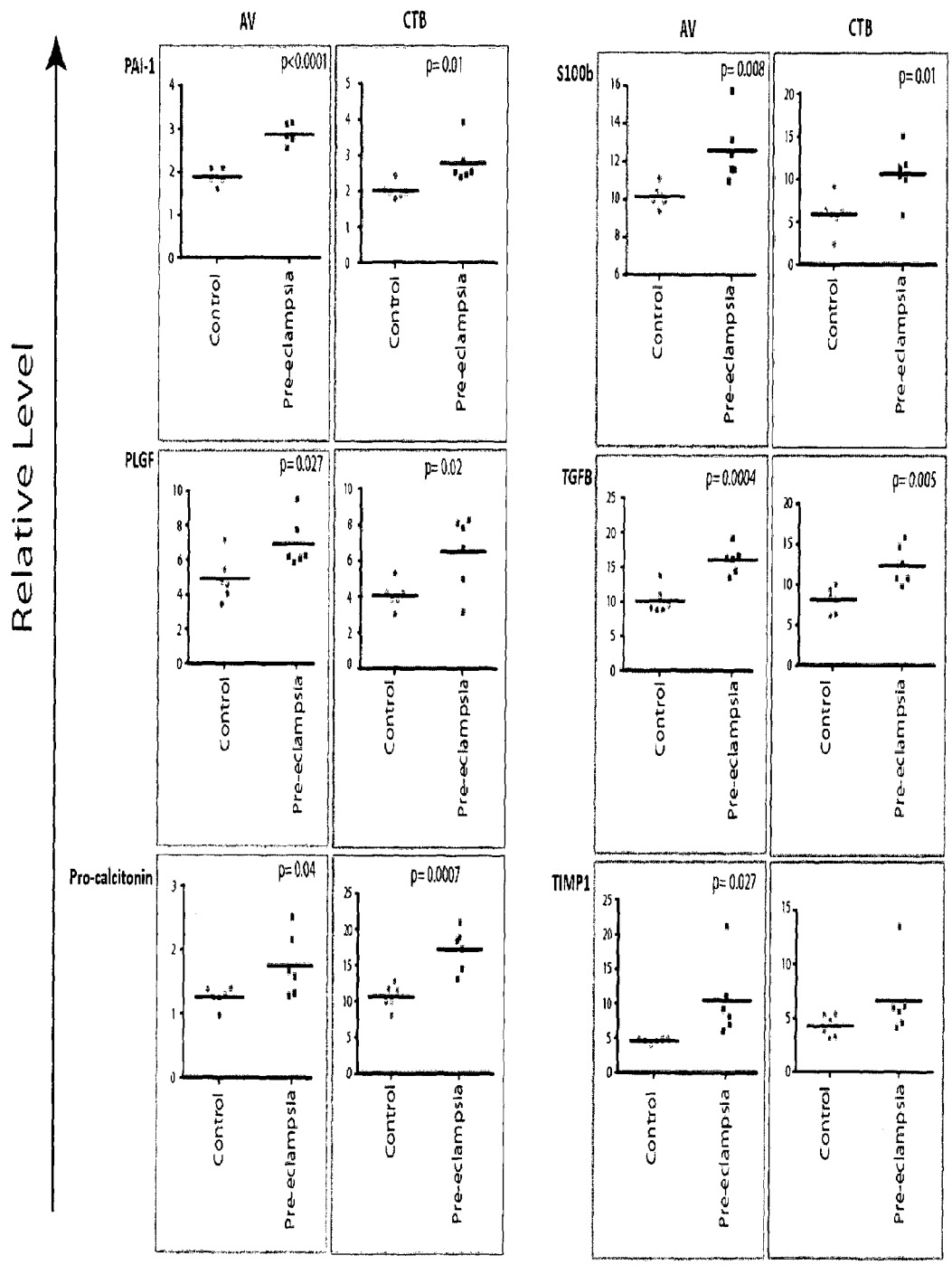

FIG. 10. Diagram showing differential distribution of proteins in annexinV-versus CTB-binding microvesicles in plasma of pregnant women (third trimester) without or with clinical diagnosis of pre-eclampsia.

DETAILED DESCRIPTION

We describe a technology to rapidly isolate different lipid microparticles found in plasma that could be used to identify and/or stratify biomarkers in different microparticle subpopulations to enhance their diagnostic, prognostic or theranostic value.

We demonstrate that CD9, a tetraspannin membrane protein stratifies into two plasma microvesicle fractions that are differentially enriched in either annexin V-binding phosphatidylserine or cholera toxin B chain (CTB)-binding GM1 ganglioside in human plasma. The affinity for annexin V and cholera toxin B chain is mutually exclusive. The association of a membrane protein with lipids suggests that these two fractions are lipid vesicles.

We also demonstrate that the relative levels of proteins or combinations of proteins in annexin V- and CTB-binding subfractions in plasma are dependent on the health or pathological status of the individuals.

We observe that the relative levels of CD9 in annexin V- and CTB-binding subfractions in healthy individuals are similar. Individuals who are ill (or at risk of illness) e.g. food poisoning or cardiac patients undergoing PCI or atherectomy have different distribution level of CD9 in these subfractions. For example, an individual with food poisoning has a higher level of CD9 in CTB-binding subfraction than that of healthy individuals while maintaining a similar level of annexin V-binding subfraction.

On the other hand, cardiac patients undergoing PCI or atherectomy have a similar level of CD9 in CTB-binding subfraction found in healthy individuals but a higher level of CD9 in annexin V-binding subfraction.

Measurement of the relative levels of proteins in annexin V- and CTB-binding subfractions in plasma may therefore be used to assess the health or pathological status of individuals.

Monitoring of States

We provide a method of monitoring the state of a cell, tissue, organ or organism.

The method may comprise establishing, for a sample of microparticles from the cell, tissue, organ or organism, a ratio of the amount of a selected polypeptide in a first type of microparticles to the amount of the selected polypeptide in a second type of microparticles.

The ratio may be a ratio of the amount of the polypeptide in the first type of microparticles as compared to the amount of the polypeptide in the second type of microparticles, i.e., between the two types of microparticles.

The first type of microparticles may be microparticles which comprise GM1 gangliosides (referred to as "GM1 ganglioside microparticles" for convenience). The first type of microparticles may be capable of binding to Cholera Toxin B (CTB), referred to as "CTB-microvesicles" for convenience.

The second type of microparticles may be microparticles which comprise exposed phosphotidylserine. The second type of microparticles may be capable of binding to Annexin V (referred to as "Annexin V microparticles" or "AV-microvesicles" for convenience).

For convenience, we refer to the presence, amount, mass or number etc of the polypeptide in the first type of microparticle, where these are GM1 ganglioside microparticles, as "GM1 ganglioside microparticle polypeptide". Similarly, for convenience, we refer to the presence, amount, mass or number etc of the polypeptide in the second type of microparticle, where these are Annexin V microparticles, as "Annexin V microparticle polypeptide". Again, for convenience, we refer to the ratio of the above as a "GM1 ganglioside microparticle polypeptide to Annexin V microparticle polypeptide ratio".

The polypeptide may be selected from the group consisting of: tetraspanin proteins (e.g. CD9, CD81, CD63) Rab GTPases (e.g Rab 5a, Rab 5b and Rab 5c, Rab-27a and Rab-27b, Rab 35), LAMP (e.g. Lamp1 and Lamp2), caveolins (e.g., caveolin 1 and caveolin 2), transferrin receptor (TRFC), Clathrin Light Chain A (CLTA), Clathrin Light Chain B (CLTB), Clathrin Heavy Chain 1 (CLTC), Tsg101, Alix, PAI-1, PLGF, Procalcitonin, S-100b, TGF beta 2 (TGFB2), TIMP1. The polypeptide may comprise CD9.

The method may be such that the microparticles comprise CD9+ microparticles. The method may be such that the microparticles comprise microvesicles, exosomes, ectosomes or apoptotic bodies.

In particular, we provide for a method of monitoring the state of a cell, tissue, organ or organism, the method comprising establishing, for a sample of microparticles from the cell, tissue, organ or organism, a ratio of: (a) a selected polypeptide in microparticles which comprise GM1 gangliosides, preferably which bind to Cholera Toxin B (CTB) ("GM1 ganglioside microparticle polypeptide"); to (b) the selected polypeptide in microparticles which comprise exposed phosphotidylserine, preferably which bind to Annexin V ("Annexin V microparticle polypeptide"); in which the (a) to (b) ratio ("GM1 ganglioside microparticle polypeptide to Annexin V microparticle polypeptide ratio") so established is indicative of the state of the cell, tissue, organ or organism; and in which the polypeptide is selected from the group consisting of: tetraspanin proteins (e.g. CD9, CD81, CD63) Rab GTPases (e.g Rab 5a, Rab 5b and Rab 5c, Rab-27a and Rab-27b, Rab 35), LAMP (e.g. Lamp1 and Lamp2), caveolins (e.g., caveolin 1 and caveolin 2), transferrin receptor (TRFC), Clathrin Light Chain A (CLTA), Clathrin Light Chain B (CLTB), Clathrin Heavy Chain 1 (CLTC), Tsg101, Alix, PAI-1, PLGF, Procalcitonin, S-100b, TGF beta 2 (TGFB2), TIMP1, preferably in which the polypeptide comprises CD9.

We further provide a method for establishing that a cell, tissue, organ or organism is in a particular state. The method may comprise comparing a GM1 ganglioside microparticle polypeptide to Annexin V microparticle polypeptide ratio of the cell, tissue, organ or organism (or a profile comprising such a ratio) with a GM1 ganglioside microparticle polypeptide to Annexin V microparticle polypeptide ratio (or a profile comprising such a ratio) of a cell, tissue, organ or organism known to be in that particular state.

In addition to, or instead of, using a single polypeptide, combinations of selected polypeptides may also be used. Accordingly, where we refer to polypeptides (e.g., by comparison of amount to establish ratios), such reference should be taken to include reference to combinations of polypeptides, for example by establishing or comparing amounts of combinations of polypeptides.

The method may comprise selecting microparticles in the sample which comprise GM1 gangliosides. This may be done for example by selecting microparticles in the sample which bind to Cholera Toxin subunit B (CTB).

The method may comprise selecting microparticles in the sample which comprise exposed phosphotidylserine. This may be done for example by selecting microparticles in the sample which bind to Annexin V.

The method may further comprise a step of selecting microparticles by size. The size selection step may comprise size exclusion chromatography. Where this is done, the size selection step may be conducted prior to the first step, e.g., step (a) above.

Where determination of an "amount" of a polypeptide is referred, it should be understood to extend to the determination or establishment of the mass, number concentration etc of the polypeptide. Where reference is made to a ratio polypeptide (or ratio of combination), being "higher" in a first state than a second state, this may be taken to mean that the ratio is statistically different in the first state compared to the second state with a p value <0.01.

The ratio so established may be indicative of the state of the cell, tissue, organ or organism.

The method may be such that the state of the cell, tissue, organ or organism comprises a physiological state, a differentiation state, a development state or a metabolic state or a pathological state, such as a disease state, a human disease state, a food poisoning state, a diabetic state, an immune disorder state, a neurodegenerative disorder state, an oncogenic state, a cancerous state or a tumour state.

For example, the state may be an Human Immunovirus (HIV) infected state, a tuberculosis (TB) infected state, a Bovine Spongiform Encephalitis (BSE) infected state, or a therapeutic state, for example, a patient undergoing treatment.

The method may be such that the state of the cell, tissue, organ or organism comprises a state of being sick, a state of poor prognosis, a state of recovery from sickness, a state of good prognosis or a healthy state.

The method may be such that the sample is selected from the group consisting of: sweat, urine, blood, tears, saliva, bronchoaveolar fluid, tumoral effusions, epididymal fluid, amniotic fluid and milk.

Where the sample is of an organism, the organism may comprise any animal or plant. The organism may comprise a mammal, such as a human.

The method may be such that it comprises any combination of the above.

Polypeptides

The polypeptide may be any suitable polypeptide whose presence, amount, mass or number etc may be determined.

Such determination may be conducted by any suitable means as known in the art, depending on the protein or polypeptide. Examples of such determination methods include mass spectrometry, spectrophotometry, UV absorption, etc.

Cholera Toxin B (CTB) may have a GenBank Accession Number ABG56900.1.

Annexin V may have a GenBank Accession Number AAB40047.1 or AAB60648.1.

The polypeptide may be selected from the group consisting of: tetraspanin proteins (e.g. CD9, CD81, CD63) Rab GTPases (e.g Rab 5a, Rab 5b and Rab 5c, Rab-27a and Rab-27b, Rab 35), LAMP (e.g. Lamp1 and Lamp2), caveolins (e.g., caveolin 1 and caveolin 2), transferrin receptor (TRFC), Clathrin Light Chain A (CLTA), Clathrin Light Chain B (CLTB), Clathrin Heavy Chain 1 (CLTC), Tsg101, Alix, PAI-1, PLGF, Procalcitonin, S-100b, TGF beta 2 (TGFB2), TIMP1. The polypeptide may comprise CD9.

CD9 may comprise a polypeptide with GenBank Accession Number NP_001760.1; CD81 may comprise a polypeptide with GenBank Accession Number NP_004347.1; CD63 may comprise a polypeptide with GenBank Accession Number NP_001771.1; Rab5a may comprise a polypeptide with GenBank Accession Number NP_004153.2; Rab5b may comprise a polypeptide with GenBank Accession Number NP_002859.1; Rab5c may comprise a polypeptide with GenBank Accession Number NP_004574.2; Rab-27a may comprise a polypeptide with GenBank Accession Number NP_004571.2; Rab-27b may comprise a polypeptide with GenBank Accession Number NP_004154.2; Rab35 may comprise a polypeptide with GenBank Accession Number NP_006852.1; Lamp1 may comprise a polypeptide with GenBank Accession Number NP_005552.3; Lamp2 may comprise a polypeptide with GenBank Accession Number NP_002285.1; Caveolin1 may comprise a polypeptide with GenBank Accession Number NP_001744.2; Caveolin2 may comprise a polypeptide with GenBank Accession Number NP_001224.1; transferrin receptor (TFRC) may comprise a polypeptide with GenBank Accession Number NP_001121620.1; Clathrin Light Chain A (CLTA) may comprise a polypeptide with GenBank Accession Number NP_001070145.1; Clathrin Light Chain B (CLTB) may comprise a polypeptide with GenBank Accession Number NP_001825.1; Clathrin Heavy Chain 1 (CLTC) may comprise a polypeptide with GenBank Accession Number NP_004850.1; Tsg101 may comprise a polypeptide with GenBank Accession. Number NP_006283.1; Alix may comprise a polypeptide with GenBank Accession Number NP_037506.2; PAI1 may comprise a polypeptide with GenBank Accession Number NP_000593.1; PLGF may comprise a polypeptide with GenBank Accession Number NP_002623.2; ProCalcitonin may comprise a polypeptide with GenBank Accession Number NP_001029124.1; S100b may comprise a polypeptide with GenBank Accession Number NP_006263.1; TGFB2 may comprise a polypeptide with GenBank Accession Number NP_001129071.1; and TIMP1 may comprise a polypeptide with GenBank Accession Number NP_003245.1.

Accordingly, we describe a method comprising selecting a polypeptide and establishing a ratio of the mass, number, amount, etc of the selected polypeptide in GM1 ganglioside microparticles compared to the selected polypeptide in Annexin V microparticles, in a sample of microparticles. The sample of microparticles may be in or of or from etc a cell, tissue, organ or organism.

Combinations of Polypeptides

As noted above, instead of, or in addition to, detection of a single polypeptide, any combination of two or more polypeptides may be used. Thus, we describe a method in which a combination of two or more polypeptides is selected and their mass, number, amount, etc detected in a first type of microparticle, as compared to their mass, number, amount, etc detected in a second type of microparticle, in a sample from or of a cell, tissue, organ or organism. The ratio so established is indicative of the state of a cell, tissue, organ or organism.

For example, combinations of any two or more of PAI-1, PLGF, Procalcitonin, S-100b, TGF beta 2, TIMP1 may be employed. We describe for example use of any one or more of: (a) PAI1 and PLGF; (b) PAI1 and Procalcitonin; (c) PAI1 and S100b; (d) PAI1 and TGFbeta2; (e) PAI1 and TIMP1; (f) PLGF and Procalcitonin; (g) PLGF and S100b; (h) PLGF and TGFbeta2; (i) PLGF and TIMP1; (j) Procalcitonin and S100b; (k) Procalcitonin and TGFbeta2; (l) Procalcitonin and TIMP1; (m) S100b and TGFbeta2; (n) S100b and TIMP1 and (o) TGFbeta2 and TIMP1, in the detection of a state comprising for example pre-eclampsia.

Polypeptide Profiles

The method may comprise establishing a profile comprising a plurality of GM1 ganglioside microparticle polypeptide to Annexin V microparticle polypeptide ratios for a plurality of selected polypeptide species. Each of the profiles may be indicative of the state of the cell, tissue, organ or organism. In other words, more than one polypeptide species may be used (i.e., ratios obtained for more than one polypeptide species).

Where reference is made to a ratio of GM1 ganglioside microparticle polypeptide to Annexin V microparticle polypeptide (or ratio of combination to combination), for example a CD9 polypeptide, being "higher" in a first state than a second state, this may be taken to mean that the ratio is statistically different in the first state compared to the second state with a p value <0.01. The same applies where amounts of combinations of polypeptides are determined.

Normalisation

The method may further comprise a step of normalisation. Such a step may comprise determining or ensuring that the quantity or concentration of any one or more proteins or polypeptides is the same across different samples.

A normalisation step, as applied to the methods and compositions described here, may make use of a polypeptide whose concentration is known to be the same across any two samples.

Accordingly, the methods described here may comprise a normalisation step. The normalisation step may comprise adjusting the level, concentration or amount of a particular polypeptide in one or more samples. The normalisation step may be conducted on two or more samples in which the level, concentration or amount of a particular polypeptide (prior to normalisation) are substantially different from each other. The normalisation step may be such that, following normalisation, the level, concentration or amount of a particular polypeptide in two or more samples are substantially the same.

The normalisation step may comprise diluting or concentrating one or other of the two samples, to increase or decrease the level, concentration or amount of a particular polypeptide in one or both samples.

Alternatively, or in addition, the normalisation step may comprise determining, for a selected two or more samples, the ratio of the levels concentration or amount of a particular polypeptide between the samples. This may be achieved by reference to a reference polypeptide which is known to have the same level, concentration or amount in each of a group of samples of interest. The reference polypeptide may comprise one or more of BNP, CD9 and TIMP-1.

It will be appreciated that, where the normalisation step comprises such determination of ratios, concentration or dilution of samples may not be needed.

Normalisation Using BNP Polypeptide

We have established that levels of BNP polypeptide in Annexin V microparticles in a cell, tissue, organ or organism that is suffering (or is at risk of suffering) from Chronic Heart Failure (CHF) disease is not statically different from levels of BNP polypeptide in a cell, tissue, organ or organism that is not suffering (or is at risk of suffering) from Chronic Heart Failure (CHF) disease, e.g., from healthy individuals.

Similarly, we have established that levels of BNP polypeptide in Annexin V microparticles in a cell, tissue, organ or organism that is suffering (or is at risk of suffering) from Acute Myocardial Ischemia (AMI) disease is not statically different from levels of BNP polypeptide in a cell, tissue, organ or organism that is not suffering (or is at risk of suffering) from Acute Myocardial Ischemia (AMI) disease, e.g., from healthy individuals.

Accordingly, the level or concentration or quantity of BNP proteins or polypeptides in in Annexin V microparticles in a cell, tissue, organ or organism may be used to normalise any of the other markers usable in the method described here, e.g., CD9 levels. Such normalisation may be effected in either Annexin V microparticles or GM1 ganglioside microparticles or both.

Normalisation Using TIMP-1 and CD 9 Polypeptide

We have established that levels of TIMP-1 polypeptide (GenBank Accession Number NP_003245.1) and CD9 polypeptide (GenBank Accession Number NP_001760.1) in GM1 ganglioside microparticles in a cell, tissue, organ or organism that is suffering (or is at risk of suffering) from Chronic Heart Failure (CHF) disease is not statically different from levels of TIMP-1 and CD9 polypeptide in a cell, tissue, organ or organism that is not suffering (or is at risk of suffering) from Chronic Heart Failure (CHF) disease, e.g., from healthy individuals.

Similarly, we have established that levels of TIMP-1 polypeptide (GenBank Accession Number NP_003245.1) and CD9 polypeptide (GenBank Accession Number NP_001760.1) in GM1 ganglioside microparticles in a cell, tissue, organ or organism that is suffering (or is at risk of suffering) from Acute Myocardial Ischemia (AMI) disease is not statically different from levels of TIMP-1 and CD9 polypeptide in a cell, tissue, organ or organism that is not suffering (or is at risk of suffering) from Acute Myocardial Ischemia (AMI) disease, e.g., from healthy individuals.

Accordingly, the level or concentration or quantity of TIMP-1 or CD9 proteins or polypeptides (or both) in GM1 ganglioside microparticles in a cell, tissue, organ or organism may be used to normalise any of the other markers usable in the method described here. Such normalisation may be effected in either Annexin V microparticles or GM1 ganglioside microparticles or both.

Establishment of Cardiovascular Disease State

We demonstrate that the GM1 ganglioside microparticle CD9 polypeptide to Annexin V microparticle polypeptide CD9 ratio of a cell, tissue, organ or organism that is suffering (or is at risk of suffering) from cardiovascular disease is higher than the cognate CD9 ratio (i.e., the GM1 ganglioside microparticle CD9 polypeptide to Annexin V microparticle polypeptide CD9 ratio) in normal or healthy cell, tissue, organ or organisms, i.e., those not suffering from cardiovascular disease.

We therefore describe a method of establishing the cardiovascular disease state of cell, tissue, organ or organism of interest, preferably an organism. Accordingly, the method described above may be such that the states of the cell, tissue, organ or organism comprise a cardiovascular disease state and a healthy state. The polypeptide may comprise CD9 in this case. The GM1 ganglioside microparticle CD9 polypeptide to Annexin V CD9 microparticle polypeptide ratio may be higher in a cardiovascular disease state compared to a healthy state. Any combination of the above may be done.

The method may comprise providing a sample of microparticles of or from the cell, tissue, organ or organism of interest. The amount of CD9 in GM1 ganglioside microparticles, i.e., microparticles which comprise GM1 gangliosides, preferably which bind to Cholera Toxin B (CTB) is established. The amount of CD9 in Annexin V microparticles, i.e., microparticles which comprise exposed phosphotidylserine, preferably which bind to Annexin V is established. The ratio between the amount of CD9 in GM1 ganglioside microparticles compared to the amount of CD9 in Annexin V microparticles is then established. This ratio is compared to the CD9 GM1 ganglioside microparticle polypeptide to Annexin V microparticle polypeptide ratio of a normal or healthy cell, tissue, organ or organism (i.e., not suffering from cardiovascular disease).

Where the ratio is higher for the cell, tissue, organ or organism of interest than the ratio from the "normal" cell, tissue, organ or organism of interest, then the cell, tissue, organ or organism of interest is determined to be suffering, or at risk of suffering from, cardiovascular disease.

Establishment of Chronic Heart Failure (CHF) State

We demonstrate that the GM1 ganglioside microparticle CD9 polypeptide to Annexin V microparticle polypeptide CD9 ratio of a cell, tissue, organ or organism that is suffering (or is at risk of suffering) from Chronic Heart Failure (CHF) disease is higher than the cognate CD9 ratio (i.e., the GM1 ganglioside microparticle CD9 polypeptide to Annexin V microparticle polypeptide CD9 ratio) in normal or healthy cell, tissue, organ or organisms, i.e., those not suffering from Chronic Heart Failure (CHF) disease.

We therefore describe a method of establishing the Chronic Heart Failure (CHF) disease state of cell, tissue, organ or organism of interest, preferably an organism. Accordingly, the method may be such that the states of the cell, tissue, organ or organism comprise a Chronic Heart Failure (CHF) disease state and a healthy state. The polypeptide may comprise CD9. The GM1 ganglioside microparticle CD9 polypeptide to Annexin V CD9 microparticle polypeptide ratio may be higher in a Chronic Heart Failure (CHF) disease state compared to a healthy state. Any combination of the above may be done.

The method may comprise providing a sample of microparticles of or from the cell, tissue, organ or organism of interest. The amount of CD9 in GM1 ganglioside microparticles, i.e., microparticles which comprise GM1 gangliosides, preferably which bind to Cholera Toxin B (CTB) is established. The amount of CD9 in Annexin V microparticles, i.e., microparticles which comprise exposed phosphotidylserine, preferably which bind to Annexin V is established. The ratio between the amount of CD9 in GM1 ganglioside microparticles compared to the amount of CD9 in Annexin V microparticles is then established. This ratio is compared to the CD9 GM1 ganglioside microparticle polypeptide to Annexin V microparticle polypeptide ratio of a normal or healthy cell, tissue, organ or organism (i.e., not suffering from Chronic Heart Failure (CHF) disease).

Where the ratio is higher for the cell, tissue, organ or organism of interest than the ratio from the "normal" cell, tissue, organ or organism of interest, then the cell, tissue, organ or organism of interest is determined to be suffering, or at risk of suffering from, Chronic Heart Failure (CHF) disease.

Establishment of Acute Myocardial Ischemia (AMI) State

We demonstrate that the GM1 ganglioside microparticle CD9 polypeptide to Annexin V microparticle polypeptide CD9 ratio of a cell, tissue, organ or organism that is suffering (or is at risk of suffering) from Acute Myocardial Ischemia (AMI) disease is higher than the cognate CD9 ratio (i.e., the GM1 ganglioside microparticle CD9 polypeptide to Annexin V microparticle polypeptide CD9 ratio) in normal or healthy cell, tissue, organ or organisms, i.e., those not suffering from Acute Myocardial Ischemia (AMI) disease.

We therefore describe a method of establishing the Acute Myocardial Ischemia (AMI) disease state of cell, tissue, organ or organism of interest, preferably an organism. The method may be such that the states of the cell, tissue, organ or organism comprise a Acute Myocardial Ischemia (AMI) disease state and a healthy state. The polypeptide may comprise CD9. The GM1 ganglioside microparticle CD9 polypeptide to Annexin V CD9 microparticle polypeptide ratio may be higher in a Acute Myocardial Ischemia (AMI) disease state compared to a healthy state. Any combination of the above may be done.

The method may comprise providing a sample of microparticles of or from the cell, tissue, organ or organism of interest. The amount of CD9 in GM1 ganglioside microparticles, i.e., microparticles which comprise GM1 gangliosides, preferably which bind to Cholera Toxin B (CTB) is established. The amount of CD9 in Annexin V microparticles, i.e., microparticles which comprise exposed phosphotidylserine, preferably which bind to Annexin V is established. The ratio between the amount of CD9 in GM1 ganglioside microparticles compared to the amount of CD9 in. Annexin V microparticles is then established. This ratio is compared to the CD9 GM1 ganglioside microparticle polypeptide to Annexin V microparticle polypeptide ratio of a normal or healthy cell, tissue, organ or organism (i.e., not suffering from Acute Myocardial Ischemia (AMI) disease).

Where the ratio is higher for the cell, tissue, organ or organism of interest than the ratio from the "normal" cell, tissue, organ or organism of interest, then the cell, tissue, organ or organism of interest is determined to be suffering, or at risk of suffering from, Acute Myocardial Ischemia (AMI) disease.

Establishment of Pre-Eclampsia State

We demonstrate that ratio of the amount of polypeptides or amounts of combinations of polypeptides in GM1 ganglioside microparticles to Annexin V microparticles of a cell, tissue, organ or organism that is suffering (or is at risk of suffering) from pre-eclampsia is higher than the cognate polypeptide/combination ratio (i.e., the ratio of the amount of polypeptides or amounts of combinations of polypeptides in GM1 ganglioside microparticles to the amount of polypeptides or amounts of combinations of polypeptides in Annexin V microparticles) in normal or healthy cell, tissue, organ or organisms, i.e., those not suffering from pre-eclampsia.

We therefore describe a method of establishing the pre-eclampsia state of cell, tissue, organ or organism of interest, preferably an organism.

Accordingly, the method described above may be such that the states of the cell, tissue, organ or organism comprise a pre-eclampsia state and a healthy state. The polypeptide may be selected from the group consisting of: PAI-1, PLGF, Pro-calcitonin, S100b, TGF$\beta$ and TIMP-1.

Any combination of two or more of the above polypeptides may be used. Such a combination may be selected from the group consisting of: PAI1 and PLGF; PAI1 and Procalcitonin; PAI1 and S100b; PAI1 and TGFbeta2; PAI1 and TIMP1; PLGF and Procalcitonin; PLGF and S100b; PLGF and TGFbeta2; PLGF and TIMP1; Procalcitonin and S100b; Procalcitonin and TGFbeta2; Procalcitonin and TIMP1; S100b and TGFbeta2; S100b and TIMP1 and TGFbeta2 and TIMP1.

The organism may comprise a pregnant organism such as a pregnant mammal, e.g., a pregnant human. The pregnant organism may be in the first trimester, second trimester or third trimester.

The GM1 ganglioside microparticle polypeptide/combination to Annexin V CD9 microparticle polypeptide/combination ratio may be higher in a pre-eclampsia state compared to a healthy state.

The method may comprise providing a sample of microparticles of or from the cell, tissue, organ or organism of interest. The amount of PAI-1, PLGF, Pro-calcitonin, S100b, TGF$\beta$ or TIMP-1, or a combination of PAI1 and PLGF; PAI1 and Procalcitonin; PAI1 and S100b; PAI1 and TGFbeta2; PAI1 and TIMP1; PLGF and Procalcitonin; PLGF and S100b; PLGF and TGFbeta2; PLGF and TIMP1; Procalcitonin and S100b; Procalcitonin and TGFbeta2; Procalcitonin and TIMP1; S100b and TGFbeta2; S100b and TIMP1 or TGFbeta2 and TIMP1 in GM1 ganglioside microparticles, i.e., microparticles which comprise GM1 gangliosides, preferably which bind to Cholera Toxin B (CTB) is established.

The amount of the selected polypeptide or combination of polypeptides in Annexin V microparticles, i.e., microparticles which comprise exposed phosphotidylserine, preferably which bind to Annexin V is also established. The ratio between the polypeptide or combination amounts in GM1 ganglioside microparticles compared to the polypeptide or combination amount of CD9 in Annexin V microparticles is then established. This ratio is compared to the GM1 ganglioside microparticle polypeptide or combination amount to Annexin V microparticle polypeptide or combination amount ratio of a normal or healthy cell, tissue, organ or organism (i.e., not suffering from pre-eclampsia).

Where the ratio is higher for the cell, tissue, organ or organism of interest than the ratio from the "normal" cell, tissue, organ or organism of interest, then the cell, tissue, organ or organism of interest is determined to be suffering, or at risk of suffering from, pre-eclampsia.

Monitoring of Changes of State

According to the methods and compositions described here, the GM1 ganglioside microparticle polypeptide to Annexin V microparticle polypeptide ratio may be used to monitor various changes of states of a cell, tissue, organ or organism.

Accordingly, we describe a method for detecting a change in state of a cell, tissue, organ or organism. The method may comprise detecting a change in a GM1 ganglioside microparticle polypeptide to Annexin V microparticle polypeptide ratio of the cell, tissue, organ or organism (or a profile comprising such a ratio). Such a change may indicate a change in state of the cell, tissue, organ or organism.

Such cell, tissue, organ or organismal changes of state may comprise changes of physiological states. The physiological state may comprise a differentiation state; in other words, the GM1 ganglioside microparticle polypeptide to Annexin V microparticle polypeptide ratio may be used to determine whether an cell, tissue, organ or organism is differentiated or un-differentiated. The physiological state may comprise a developmental state or developmental stage.

Thus, the GM1 ganglioside microparticle polypeptide to Annexin V microparticle polypeptide ratio may be used to determine if a cell, tissue, organ or organism is of or from an embryonic state or stage, foetal state or stage, a neonatal state or stage, an infant state or stage, a juvenile state or stage, a toddler state or stage, an adolescent state or stage, an adult state or stage etc.

The GM1 ganglioside microparticle polypeptide to Annexin V microparticle polypeptide ratio of a cell, tissue, organ or organism may be monitored or tracked over time intervals to establish or monitor or detect changes of state.

It will be understood that, where reference is made to establishing or determining the state of a cell, tissue, organ or organism, this will be understood to encompass establishing or determining the state, per se, as well as establishing or determining whether or not (and the extent of) cell, tissue, organ or organism being at risk of transitioning or going into that state. In other words, establishment of state includes establishment of risk of entering or suffering from that state.

Detecting and Treating Disease

We describe a method of detecting a disease in a cell, tissue, organ or organism, the method comprising obtaining a sample from or of that cell, tissue, organ or organism, performing a method as set out above on the sample, and comparing the GM1 ganglioside microparticle polypeptide to Annexin V microparticle polypeptide ratio thereby obtained with a GM1 ganglioside microparticle polypeptide to Annexin V microparticle polypeptide ratio of a sample known to be of or from a diseased cell, tissue, organ or organism.

We further describe a method of treatment or prevention of a disease in a cell, tissue, organ or organism, the method comprising detecting a disease in a cell, tissue, organ or organism as set out above, and administering a treatment for that disease to the cell, tissue, organ or organism.

The method may be such that the sample is selected from the group consisting of: urine, blood, tears, saliva, bronchoaveolar fluid, tumoral effusions, epididymal fluid, amniotic fluid and milk.

The method may be such that the microparticles comprise microvesicles, exosomes, ectosomes or apoptotic bodies.

Microparticles

The microparticle may in particular comprise a vesicle such as a microvesicle. The microparticle may comprise an exosome.

The microparticle may comprise a vesicle or a flattened sphere limited by a lipid bilayer. The microparticle may comprise a diameter of 40-100 nm. The microparticle may be formed by inward budding of the endosomal membrane. The microparticle may have a density of ~1.13-1.19 g/ml and may float on sucrose gradients. The microparticle may be enriched in cholesterol and sphingomyelin, and lipid raft markers such as GM1, GM3, flotillin and the src protein kinase Lyn.

Methods of isolating microparticles are known in the art and are described in detail in the Examples below, as well as in documents such as International Patent Publication WO 2009/105044.

We describe in particular a technology to rapidly isolate different lipid microparticles found in plasma that could be used to identify and/or stratify biomarkers in different microparticle sub-populations to enhance their diagnostic, prognostic or theranostic value.

We therefore provide a method of treating a sample containing microparticles, the method comprising: (a) selecting microparticles in the sample which comprise GM1 gangliosides; and/or (b) selecting microparticles in the sample which comprise exposed phosphotidylserine.

The method may be such that step (a) comprises selecting microparticles in the sample which bind to Cholera Toxin subunit B (CTB); or in which step (b) comprises selecting microparticles in the sample which bind to Annexin V, or both.

The method may be such that it further comprises a step of selecting microparticles by size, for example, by size exclusion chromatography.

The method may be such that the microparticles comprise CD9+ microparticles.

Specifically, we provide a method to rapidly isolate annexin V- and CTB-binding subfractions of lipid microparticles from plasma for the detection of microparticle-associated proteins. Rapid isolation of annexin V- and CTB-binding subfractions lipid microparticle subpopulations could provide a means to stratify known disease biomarkers further into more defined plasma subfractions and improve their diagnostic, prognostic or theranostic values.

We provide a method for fractionating a sample containing microparticles. The method may comprise selecting an Annexin V-subfraction of microparticles or a CTB-binding sub-fraction of microparticles, or both. The method may comprise performing a method as set out above.

The method may further comprise the step of detecting and/or quantitating a membrane protein or a luminal protein, or both, in a fractionated sample of microparticles.

We provide a purified sample of microparticles, in which: (a) substantially all microparticles in the sample are capable of binding to cholera toxin B (CTB) but not to Annexin V; or (b) substantially all microparticles in the sample are capable of binding to Annexin V but not to cholera toxin B (CTB).

Monitoring of Pathological States

The cell, tissue, organ or organismal state may comprise a pathological state, such as a disease state. Thus, the GM1 ganglioside microparticle polypeptide to Annexin V microparticle polypeptide ratio may be used to monitor a pathological state of a cell, tissue, organ or organism, or a change of a normal state to a pathological state.

The GM1 ganglioside microparticle polypeptide to Annexin V microparticle polypeptide ratio may be used to detect whether the cell, tissue, organ or organism is in a normal (undiseased) state or a diseased state. It may be used to monitor the progression of a cell, tissue, organ or organism from a normal, undiseased state to a diseased state. It may be used to monitor the stage of disease of the cell, tissue, organ or organism. The disease may comprise any of the variety of diseases a cell, tissue, organ or organism suffers or may suffer.

In general, the disease state may comprise any one or more of hypertrophic cardiomyopathy, bacterial endocarditis, agyria, amyotrophic lateral sclerosis, dizziness, tetralogy of fallot, myocarditis, alcoholism, anemia, brachial plexus, neuropathies, hemorrhoids, congenital heart defects, alopecia greata, sickle cell anemia, mitral valve prolapse, autonomic nervous system diseases, abnormalities, alzheimer disease, angina pectoris, rectal diseases or arrhythmogenic right.

The disease state may comprise any one or more of ventricular dysplasia, acne rosacea, amblyopia, ankylosing spondylitis, atrial fibrillation, cardiac tamponade, acquired immunodeficiency syndrome, amyloidosis, anorexia, anxiety, autism, brain neoplasms, central nervous system diseases, color vision defects, arteriosclerosis, back pain, breast diseases, central nervous system infections, colorectal neoplasms, arthritis, behcet's syndrome, breast neoplasms, cerebral palsy, common cold, asthma, bipolar disorder, burns or cervix neoplasms.

The disease state may comprise any one or more of communication disorders, atherosclerosis, blindness, candidiasis, charcot-marie disease, crohn disease, attention deficit disorder, brain injuries, cataract, ulcerative colitis, cumulative trauma disorders, cystic fibrosis, developmental disabilities, eating disorders, erysipelas, fibromyalgia, decubitus ulcer, diabetes, emphysema, *escherichia coli* infections, folliculitis, deglutition disorders, diabetic foot or encephalitis.

The disease state may comprise any one or more of esophageal diseases, food hypersensitivity, dementia, down syndrome, japanese encephalitis, eye neoplasms, food poisoning, dengue, dyslexia, endometriosis, fabry's disease, gastroenteritis, depression, dystonia, epilepsy, chronic fatigue syndrome, gastroesophageal reflux, gaucher's disease, hematologic diseases, hirschsprung disease, hydrocephalus, hyperthyroidism, gingivitis, hemophilia, histiocytosis, hyperhidrosis, hypoglycemia, glaucoma, hepatitis and hiv infections. For example, the state may be an Human Immunovirus (HIV) infected state, a tuberculosis (TB) infected state, a Bovine Spongiform Encephalitis (BSE) infected state, or a therapeutic state, for example, a patient undergoing treatment.

The disease state may comprise any one or more of hyperoxaluria, hypothyroidism, glycogen storage disease, hepatolenticular degeneration, hodgkin disease, hypersensitivity, immunologic deficiency syndromes, headache, hernia, holt-oram syndrome, hypertension, impotence, congestive heart failure, herpes genitalis, huntington's disease, pulmonary hypertension, incontinence, infertility, leukemia, systemic lupus erythematosus, maduromycosis, mental retardation, inflammation, liver neoplasms, lyme disease, malaria or inborn errors of metabolism.

The disease state may comprise any one or more of inflammatory bowel diseases, long qt syndrome, lymphangiomyomatosis, measles, migraine, influenza, low back pain, lymphedema, melanoma, mouth abnormalities, latex allergy, obstructive lung diseases, lymphoma, meningitis, mucopolysaccharidoses or leprosy.

The disease state may comprise any one or more of lung neoplasms, macular degeneration, menopause, multiple sclerosis, muscular dystrophy, myofascial pain syndromes, osteoarthritis, pancreatic neoplasms, peptic ulcer, myasthenia gravis, nausea, osteoporosis, panic disorder, persian gulf syndrome, myeloma, acoustic neuroma, otitis media, paraplegia, phenylketonuria, myeloproliferative disorders, nystagmus, ovarian neoplasms or parkinson disease.

The disease state may comprise any one or more of pheochromocytoma, myocardial diseases, opportunistic infections, pain, pars planitis, phobic disorders, myocardial infarction, hereditary optic atrophy, pancreatic diseases, pediculosis, plague, poison ivy dermatitis, prion diseases, reflex sympathetic dystrophy, schizophrenia, shyness, poliomyelitis, prostatic diseases, respiratory tract diseases, scleroderma, sjogren's syndrome or polymyalgia rheumatica.

The disease state may comprise any one or more of prostatic neoplasms, restless legs, scoliosis, skin diseases, postpoliomyelitis syndrome, psoriasis, retinal diseases, scurvy, skin neoplasms, precancerous conditions, rabies, retinoblastoma, sex disorders, sleep disorders, pregnancy, rare diseases, sarcoidosis, sexually transmitted diseases, spasmodic torticollis or spinal cord injuries.

The disease state may comprise any one or more of stuttering, testicular neoplasms, trichotillomania, urinary tract, infections, spinal dystaphism, substance-related disorders, thalassemia, trigeminal neuralgia, urogenital diseases, spinocerebellar degeneration, sudden infant death, thrombosis, tuberculosis, vascular diseases, strabismus, suicide, tinnitus, tuberous sclerosis, virus diseases, post-traumatic stress disorders, syringomyelia, tourette syndrome, turner's syndrome or vision disorders.

The disease state may comprise any one or more of psychological stress, temporomandibular joint dysfunction syndrome, trachoma, urinary incontinence, vomiting, von willebrand's disease, renal osteodystrophy, bacterial infections, digestive system, neoplasms, bone neoplasms, vulvar diseases, ectopic pregnancy, tick-borne diseases, marfan syndrome, aging, williams syndrome, angiogenesis factor, urticaria, sepsis, malabsorption syndromes or wounds and injuries.

The disease state may comprise any one or more of cerebrovascular accident, multiple chemical sensitivity, dizziness, hydronephrosis, yellow fever, neurogenic arthropathy, hepatocellular carcinoma, pleomorphic adenoma, vater's ampulla, meckel's diverticulum, keratoconus skin, warts, sick building syndrome, urologic diseases, ischemic optic neuropathy, common bile duct calculi, otorhinolaryngologic diseases, superior vena cava syndrome, sinusitis, radius fractures, osteitis deformans, trophoblastic neoplasms, chondrosarcoma or reading and carotid stenosis.

The disease state may comprise any one or more of varicose veins, creutzfeldt-jakob syndrome, gallbladder diseases, replacement of joint, vitiligo, nose diseases, environmental illness, megacolon, pneumonia, vestibular diseases, cryptococcosis, herpes zoster, fallopian tube neoplasms, infection, arrhythmia, glucose intolerance, neuroendocrine tumors, scabies.

The disease state may comprise any one or more of alcoholic hepatitis, parasitic diseases, salpingitis, cryptococcal meningitis, intracranial aneurysm, grief, calculi, pigmented nevus, rectal neoplasms, mycoses, hemangioma, colonic neoplasms, hypervitaminosis a, nephrocalcinosis, kidney neoplasms, vitamins, carcinoid tumor, celiac disease, pituitary diseases, brain death, biliary tract diseases or prostatitis.

The disease state may comprise any one or more of iatrogenic disease, gastrointestinal hemorrhage, adenocarcinoma, toxic megacolon, amputees, seborrheic keratosis, osteomyelitis, barrett esophagus, hemorrhage, stomach neoplasms, chickenpox, cholecystitis or chondroma.

The disease state may comprise any one or more of bacterial infections and mycoses, parathyroid neoplasms, spermatic cord torsion, adenoma, lichen planus, anal gland neoplasms, lipoma, tinea pedis, alcoholic liver diseases, neurofibromatoses, lymphatic diseases, elder abuse, eczema, diverticulitis, carcinoma, pancreatitis, amebiasis, pregnancy complications, pyelonephritis, infectious mononucleosis or aneurysm.

The disease state may comprise pre-eclampsia, for example in a pregnant organism such as a pregnant human woman. The pregnant organism may be in the first trimester of pregnancy, the second trimester of pregnancy or the third trimester of pregnancy. A sample may be taken of a pregnant woman in the third trimester of pregnancy, for example, and subjected for analysis as described in this document to establish whether she is, or is at risk of suffering from pre-eclampsia.

In particular, the disease state may comprise a disease such as diabetes, immune disorders, neurodegenerative disorders or cancers or tumours. Thus, the GM1 ganglioside microparticle polypeptide to Annexin V microparticle polypeptide ratio may be used to monitor the state of a cell, tissue, organ or organism which is suffering, or is prone to suffering, any of the diseases listed above.

Monitoring of Recovery

Protein levels, including plasma CD9 levels, may be monitored in the two different microparticle populations (viz, annexin V- and CTB-binding subfractions) in a single individual—e.g., during an episode of food poisoning—to monitor the injury, recovery and baseline in a patient.

The level of CD9 in one population may indicate tissue injury, while the level of CD9 in the other may indicate tissue repair. By measuring the relative levels of these two populations, it can be determined if a patient has more tissue injuries (i.e. sick, poor prognosis), has initiated tissue repair (i.e. recovering, good prognosis) or is in good health.

The ratio of GM1 ganglioside microparticle polypeptide to Annexin V microparticle polypeptide may also be used to indicate prognosis of the patient.

Biological Sample

The methods and compositions described here involve the ratio of GM1 ganglioside microparticle polypeptide to Annexin V microparticle polypeptide secreted by a cell in order to monitor its state. Conveniently, the ratio may be determined by taking a biological sample comprising secretions of the cell.

Where the cell is comprised in an organism, the sample may comprise any number of things, including, but not limited to, bodily fluids (including, but not limited to, blood, nasopharyngeal secretions, urine, serum, lymph, saliva, anal and vaginal secretions, perspiration and semen, of virtually any organism.

Preparation of Microparticles

CTB or Annexin V binding microparticles may be prepared from plasma (or other fluids) using the following protocol:

10 µL plasma were incubated with 0.1 ng biotinylated Cholera Toxin subunit B (CTB) (SBL Vaccin AB) or 0.1 ng biotinylated Annexin V (AV) (BioVision) in 100 µL PBS pH 7.4 for 1 hour at 37° C. with shaking at 800 rpm. In the meantime, 100 µL of Dynabeads® M-280 Streptavidin (Invitrogen) was washed three times with 100 µL PBS. After the last wash, the plasma-CTB or plasma-AV reaction mix was added to the washed beads and incubated with shaking at 800 rpm for 30 minutes. The beads were immobilised with a magnet and the supernatant was removed. The beads were then washed thrice with 200 µl PBS and the washes were removed each time after immobilizing the beads with a magnet.

GM1 Ganglioside Microparticle Polypeptide to Annexin V Microparticle Polypeptide Ratio The GM1 ganglioside microparticle polypeptide to Annexin V microparticle polypeptide ratio may be simply calculated as a ratio of the quantity of polypeptide in GM1 ganglioside microparticles to the quantity of polypeptide in Annexin V microparticles.

Alternatively, or in addition, the quantity of another polypeptide in GM1 ganglioside microparticles to, the quantity of that polypeptide in Annexin V microparticles known not to be changed as a result of the change in cellular state may be used as an internal control.

Thus, instead of, or in addition to, monitoring the change in the GM1 ganglioside microparticle polypeptide to Annexin V microparticle polypeptide ratio, the ratio of a first ratio against a second ratio may be used for monitoring purposes. Here, the first ratio is the ratio of GM1 ganglioside microparticle polypeptide to Annexin V microparticle polypeptide known to be changed as a result of the change in cellular state and the second ratio being the ratio GM1 ganglioside microparticle polypeptide to Annexin V microparticle polypeptide ratio known not to be changed as a result of the change in cellular state.

GM1 Ganglioside Microparticle Polypeptide to Annexin V Microparticle Polypeptide Ratio Profile Alternatively or in addition to determining the ratio of GM1 ganglioside microparticle polypeptide to Annexin V microparticle polypeptide, a profile comprising a plurality of GM1 ganglioside microparticle polypeptide to Annexin V microparticle polypeptide ratios for a plurality of selected polypeptide species, each indicative of the state of the cell, may also be established. Changes to such a profile may be monitored as a means to monitor the state of a cell. The profile may be established by any means known in the art, such as by hybridisation to an array comprising a plurality of binding agents capable of binding to and distinguishing between each of the plurality of the selected polypeptide species.

EXAMPLES

Example 1

Enrichment of CD9+ Microparticles from Serum of Normal Individuals

In this study, we first determined if CTB will bind CD9+ microparticles in serum. As there were no CTB-bound CD9, we determined the sedimentation density of serum CD9+ microparticles in a sucrose density gradient and found the CD9 in the serum to have a higher sedimentation density than that for exosomes.

The lack of CTB binding and the high sedimentation density suggested that the CD9+ microparticles were apoptotic bodies. This was then confirmed by the binding of serum CD9 to annexin V.

Example 2

Materials and Methods—Size Exclusion Chromatography 2 mL Sepharose 2B resins (Sigma Aldrich, Cat no. 2B300) was pipetted into a spin column (Bio-Rad, Cat no. 732-6008) and spun d at 800 g for 1 minute. The supernatant was removed and washed by adding 1 mL Phosphate Buffer Saline (PBS) followed by a 1-minute spin at 800 g. 1 mL of human serum was then loaded and the column was spun at 800 g for 1 minute.

The flow through was collected and this process was repeated thrice using 1 mL of PBS each time. 3 wash fractions were collected. 20 µL of each fraction was resolved on a 4-12% SDS/polyacrylamide gels. The gels were either stained with SilverQuest™ Silver Staining Kit (Invitrogen, Carlsbad, Calif.) or electroblotted onto a nitrocellulose membrane. The membrane was probed with either a 1:50 dilution of mouse anti-human CD9 antibody followed by a 1:1250 dilution of a HRP-conjugated donkey anti-mouse IgG antibody.

All antibodies were purchased from Santa Cruz. The bound antibodies were visualized using HRP-enhanced chemiluminescent substrate (Thermo Fisher Scientific Inc., Waltham, Mass.) and exposure to an X-ray film.

Example 3

Materials and Methods—Cholera Toxin B Affinity Chromatography

200 µL of serum flow through from the size exclusion were incubated with 0.1 µg biotinylated Cholera Toxin subunit B (CTB) (Invitrogen) in 100 µL PBS pH 7.4 for 1 hour at room temperature with shaking at 800 rpm. After washing 100 µl of Dynabeads® M-280 Streptavidin (Invitrogen) three times with 100 μl PBS, the reaction mix was added and incubated with shaking at 800 rpm for 30 mins.

The beads were immobilised with a magnet and the supernatant or unbound fraction was removed. The beads were then washed twice with 100 μl PBS and the washes were removed each time after immobilizing the beads with a magnet. The beads were boiled in 100 μl of a denaturing/reducing SDS-PAGE loading buffer to elute the remaining bound proteins. Equal volume of the unbound fraction, washes, eluted and bound fraction was resolved on 4-12% SDS-polyacrylamide gels.

The gels were either stained with silver or electroblotted onto a nitrocellulose membrane. The membrane was probed with 1:50 dilution of mouse anti-human CD9 antibody. The secondary antibody was 1:1250 of HRP conjugated donkey anti-mouse Ig G antibody. All antibodies were purchased from Santa Cruz. The bound antibodies were visualized using HRP-enhanced chemiluminescent substrate (Thermo Fisher Scientific Inc., Waltham, Mass.) and exposure to an X-ray film.

Example 4

Materials and Methods—Sucrose Gradient 14 sucrose solutions with concentrations from 22.8% to 60% were prepared and layered sequentially in an ultracentrifuge tube (Beckman Coulter Inc., CA) starting with the most concentrated solution. 500 μL of the human serum was loaded on top before ultracentrifugation for 16.5 h at 200 000 g, 4° C. in a SW60Ti rotor (Beckman Coulter Inc.). After centrifugation, 320 μL of 13 fractions were collected starting from the top of the gradient.

The densities of each fractions were determined by weighing a fixed volume. 20 pt of each fractions was resolved on 4-12% SDS-polyacrylamide gels. The gels were either stained with SilverQuest™ Silver Staining Kit (Invitrogen, Carlsbad, Calif.) or electroblotted onto a nitrocellulose membrane. The membrane was probed with either a 1:50 dilution of mouse anti-human CD9 antibody followed by a 1:1250 dilution of a HRP-conjugated donkey anti-mouse IgG antibody. All antibodies were purchased from Santa Cruz.

The bound antibodies were visualized using HRP-enhanced chemiluminescent substrate (Thermo Fisher Scientific Inc., Waltham, Mass.) and exposure to an X-ray film. Fractions 9 to 13 from the sucrose gradient were pooled and dialysed against PBS pH7.4 overnight. The pooled fractions were concentrated to 20 μL Example 5

Materials and Methods—Annexin V Affinity Chromatography

20 μL of the pooled fractions from the sucrose gradient was mixed with 20 μL of 5× Annexin V binding buffer (Calbiochem) and made up to a final volume of 100 μL with water. 90 μL of the pooled fraction sample was incubated with 10 μL of Annexin V for 1 hour at room temperature with shaking at 800 rpm.

After washing 100 μl of Dynabeads® M-280 Streptavidin (Invitrogen) three times with 100 μl PBS, the reaction mix was added and incubated with shaking at 800 rpm for 30 mins. The beads were immobilised with a magnet and the supernatant or unbound fraction was removed. The beads were then washed four times with 100 μl PBS and the washes were removed each time after immobilizing the beads with a magnet.

The beads were boiled in 100 μl of a denaturing/reducing SDS-PAGE loading buffer to elute the remaining bound proteins. Equal volume of the unbound fraction, washes, eluted and bound fraction was resolved on 4-12% SDS-polyacrylamide gels. The gels were electroblotted onto a nitrocellulose membrane.

The membrane was probed with 1:50 dilution of mouse anti-human CD9 antibody. The secondary antibody was 1:1250 of HRP conjugated donkey anti-mouse IgG antibody. All antibodies were purchased from Santa Cruz.

The bound antibodies were visualized using HRP-enhanced chemiluminescent substrate (Thermo Fisher Scientific Inc., Waltham, Mass.) and exposure to an X-ray film.

Example 6

CD9 in Serum of Healthy Individuals Binds to Annexin V but not CTB

To determine if CD9+ microparticles are present in the serum of healthy individuals CTB, the serum was first size fractionated to enrich for large particles and remove abundant small serum proteins such as albumin. The fractionated serum was then incubated CTB to determine if CD9 in the serum binds to with annexin V or annexin V.

Example 7

Figure 1:
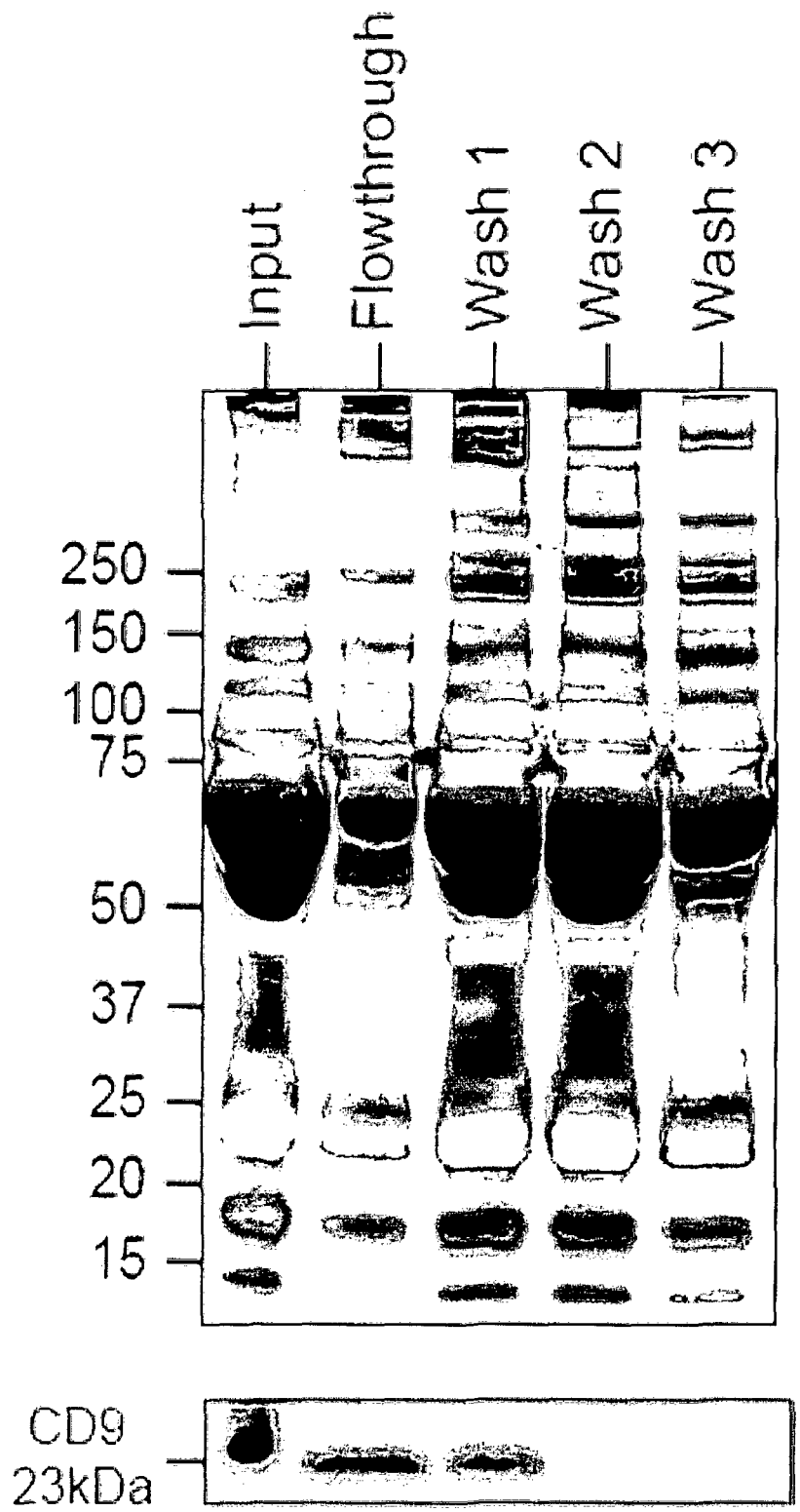
FIG. 1 is a diagram showing size fractionation of serum. Serum from healthy individuals was passed through a sepharose 2B size exclusion spin column. The column was washed 3 times with PBS.

Results—Large CD9+ Microparticles are Present in Serum of Healthy Individuals by CTB The results are shown in FIG. 1.

Size fractionation of the serum resulted in the enrichment of CD9 in the flow through and wash 1 fraction suggesting that CD9, a small protein must be associated with a large complex.

Example 8

Results—CD9+ Microparticles do not Bind CTB

The results are shown at the top panel of FIG. 2.

Most of the proteins did not bind to the CTB including CD 9 (lower panel). Therefore, CD9+ microparticles in serum of healthy individuals did not bind CTB and did not have GM1 gangliosides. CD9+ microparticles in serum of healthy individuals are not exosomes.

Example 9

Results—CD9+ Microparticles have a High Sedimentation Density

The results are shown in FIG. 3.

To identify the type of CD9+ microparticles in serum of healthy individuals, the serum was fractionated on a sucrose density gradient and fractions were analysed by SDS/PAGE and western blot hybridization. CD9+ microparticles sedimented at a density of 1.181-1.226 g/ml. This density is the expected density of apoptotic bodies and not of exosomes which is 1.13-1.19 g/ml and (Thery, Ostrowski et al. 2009).

Example 10

Results—CD9+ Microparticles in Serum of Healthy Individuals Bind Annexin V

The results are shown in FIG. 4.

To confirm that some of CD9+ microparticles were apoptotic bodies, we determine if these microparticles could bind annexin V. Some of the dense CD9+ microparticles but not all could bind annexin V as CD9 was detected only when 10 more of the bound fraction was loaded onto the gel.

Example 11

Conclusions

Serum of healthy individuals contains CD9+ microparticles. However these microparticles are not exosomes or a very small proportion of these microparticles was exosomes. They do not bind CTB and therefore have little or no GM1 gangliosides or lipids highly enriched in lipid rafts, a hallmark feature of exosome membrane.

Furthermore, most, if not all of these microparticles are dense microparticles with sedimentation density in sucrose of 1.181-1.226 g/ml and not the 1.13-1.19 g/ml density of exosomes. Instead a significant proportion was dense apoptotic bodies that contain exposed PS. The remaining microparticles could still be apoptotic bodies but this needs to be verified. The low level of CTB-binding CD9+ microparticles in serum of healthy individuals will increase the predictability of any biomarkers of disease or disease susceptibility that are derived from CTB-binding CD9+ microparticles in serum.

Given that exosomes are secreted as a vehicle of intercellular communication in neurons and immune cells (Smalheiser 2007; Thery, Ostrowski et al. 2009) and many disease-associated proteins have been reported to be secreted in exosomes e.g. beta-amyloid peptides in Alzheimer's disease (Rajendran, Honsho et al. 2006), mycobacterial proteins in *M. tuberculosis*-infected J774 cells (Giri, Kruh et al. 2010), tumor antigens (Taylor and Gercel-Taylor 2005), our observation of a low baseline of CTB-binding CD9+ microparticles in serum of healthy individuals may an indicator of relative good health and a rise may be a sentinel of disease, disease injury or increased cellular communication for tissue repair.

Analysis of this population of microparticles is therefore likely to yield more predictive biomarker to diagnose or prognose diseases.

Example 12

Differences Between Lipid Microvesicles in Plasma and MSC-Conditioned Medium

Materials and Methods

Culture medium conditioned by Myc-transformed ES-derived MSC line (Myc-HuES9.E1) and plasma were loaded onto a sucrose density gradient. The gradient was prepared by layering 14 sucrose solutions of concentrations from 23% to 60% (w/v).

After loading the samples, the gradient was ultracentrifuged for 18 h at 200,000 g, 4° C. The gradient was removed from the top in 13 fractions. The density of each fraction was determined by weighing 100 µL of each fraction. The relative level of CD9+ annexin V-binding microvesicles and CD9+ CTB-binding microvesicles in each fraction were determined.

Results

Please refer to FIG. 5.

CD9+ microvesicles in plasma are predominantly annexin V-binding while those in MSC-conditioned medium are predominantly cholera toxin B-chain (CTB) binding.

CTB-binding microvesicles in plasma float at two distinctive sucrose densities 1.21-1.59 and >1.173 g/ml while CTB-binding microvesicles float at one density i.e. 1.065-1.191 g/ml Note: CD81+ microvesicles in the plasma and MSC-conditioned medium exhibit the same distribution profile as CD9+ microvesicles.

Example 13

Distribution of Proteins in Annexin V-Versus CTB-Binding Microvesicles in Plasma of Cardiac Patients and Healthy Individuals Materials and Methods Please refer to FIG. 6A and FIG. 6B.

Plasma from healthy individuals (H) and cardiac patients (D) were incubated with biotinylated Annexin V (FIG. 6A) or Cholera Toxin B (FIG. 6B). Microvesicles that bind either Annexin V or Cholera Toxin B were extracted with streptavidin-conjugated magnetic beads. Proteins in these isolated microvesicles were assayed using specific antibody in an ELISA.

Results

Some proteins in annexin V- and CTB-binding plasma microvesicles are differentially distributed between healthy individuals and patients at a cardiac clinic e.g.

CD9, CD81 and TIMP1 in annexin V-binding but not CTB-binding plasma microvesicles are significantly higher in patients than in healthy individuals;

ANP in CTB-binding but not annexin V-binding plasma microvesicles is significantly higher in patients than in healthy individuals The other proteins may exhibit a significantly different distribution profile in the two types of microvesicles of patients vs healthy individuals if population size is bigger, and/or the disease is more narrowly defined.

Other biomarkers that could be used to assess differences in plasma microvesicles of cardiac patients versus healthy individuals are BNP, endothelin, rennin, angiotensin troponin, myosin, IL6, IL1, IL10, TNFα, TGFβ.

Example 14

Distribution of Proteins in Annexin V-Versus CTB-Binding Microvesicles in Plasma of Patients with Chronic Heart Failure (CHF) and Patients with Acute Myocardial Ischemia (AMI)

To evaluate the feasibility and value of being able to fractionate plasma microvesicle for biomarker assay, we applied this technology to plasma samples from more defined patient groups: Patients with chronic heart failure (CHF) and patients with acute myocardial ischemia (AMI). The controls are plasma from healthy individuals (con) (FIG. 7).

Materials and Methods

For each biomarker in either microvesicle A or B, five to ten microliters of plasma from heart failure patients (CHF), healthy individuals (Con) and AMI patients (AMI) were used.

The relative levels of BNP, Flt-1, TIMP-1, CD9 and ANP in either microvesicle A or B were determined by first isolating the microvesicle by affinity chromatography followed by an ELISA using antibody specific for the ligand. Flt-1 and CD9 are membrane bound proteins while BNP, TIMP-1 and ANP are luminal proteins.

The distribution of these proteins in microvesicle A or B of the different groups of patients were analysed. CHF and AMI patients had significantly higher BNP level in microvesicle B but not A, relative to Con individuals. Flt-1 in both microvesicle A and B was higher for AMI patients to Con individuals.

However, Flt-1 in microvesicle A was lower for CHF patients and that in microvesicle B was not significantly different from Con individuals. Among the microvesicles in the three patient groups, only microvesicle A-associated TIMP-1 in CHF patients was significantly different i.e. higher.

CD9 in microvesicle A but not B was significantly higher in CHF and AMI patients. ANP in microvesicle A was significantly higher for CHF and AMI patients. In microvesicle B, ANP A was significantly higher only for AMI patients.

Results

Please refer to FIG. 7.

Microvesicles isolated by affinity to either CTB or annexin (FIG. 7) are different from each other as demonstrated by their different protein profile (FIG. 7). The differences are also disease specific. For example, BNP level in the annexin V-bound microvesicle fraction of the CHF, AMI and con was not significantly different in all three patient groups.

However, BNP level in the CTB-bound microvesicle fraction of the CHF and AMI was significantly higher than control. On the other hand, ANP in the Annexin (FIG. 7) fraction was significantly higher in both CHF and AMI groups compared to the con group but ANP in the CTB fraction was significantly higher only in the AMI group.

Example 15

Monitoring Plasma CD9 of a Case of Food Poisoning

Plasma from an individual with food poisoning was analysed as described above during and 3 weeks after the event. Two plasma samples from an healthy individual taken three weeks apart served as control.

The results are shown in FIG. 8. The average fluorescence in the CTB fraction and AnnV faction for patient before (A1) and three weeks after food poisoning (A2) were plotted against those of B1 and B2. B1 and B2 were the plasma samples taken three weeks apart from a healthy control.

Example 16

Development of an Assay to Couple the Isolation of Either CTB or Annexin V Binding Microvesicles to the Quantification of Membrane and Luminal Proteins in the Microvesicles Materials and Methods Please refer to FIG. 9.

Plasma is first incubated with biotinylated CTB and then with streptavidin-conjugated magnetic beads. The magnetic beads are then immobilized with a magnet and washed with PBS or a isotonic salt solution. Bound microvesicles are lysed with a generic detergent-based cell lysis buffer.

The microvesicle contents are then biotinylated by activated biotin e.g. sulfo-NHS-Biotin. To assay for a specific protein, magnetic bead conjugated antibody specific for the protein of interest is then added. The antibody-bound protein is then immobilized by magnet and washed extensively.

The protein is quantified using streptavidin-conjugated HRP and a HRP colorimetric or fluorimetric substrate.

Example 17

Conclusion

The technology could quantitatively assay for both membrane and luminal proteins in the isolated microvesicles—we could detect both membrane and luminal proteins (FIG. 7). The method for detecting both membrane and luminal proteins are schematically depicted in FIG. 8.

Example 18

Differential Distribution of Proteins in AnnexinV-Versus CTB-Binding Microvesicles in Plasma of Pregnant Women (Third Trimester) without or with Clinical Diagnosis of Pre-Eclampsia—Single Polypeptides For each biomarker in either AnnexinV (AV)- or cholera toxin B chain (CTB)-binding microvesicles (see Tables E1 and E2 below), five to ten microliters of plasma from third trimester pregnant women without pre-eclampsia (control) and with clinically diagnosed pre-eclampsia (Pre-eclampsia).

The relative levels of PAI-1, PLGF, Pro-calcitonin, S100b, TGFβ and TIMP-1 in either AnnexinV (AV)- or cholera toxin B chain (CTB)-binding microvesicles were measured as described below.

Briefly, AV- or CTB-binding microvesicles were first isolated by affinity chromatography, the isolated microvesicles were lysed to release proteins associated with the microvesicle and the released proteins were then biotinylated. The targeted protein of interest was then assayed using a specific antibody conjugated to HRP and a fluorescent HRP substrate.

FIG. 10 demonstrates that PAI-1, PLGF, Pro-calcitonin, S100b, TGFβ and TIMP-1 in annexinV- and/or CTB-binding microvesicles in plasma of pregnant women (third trimester) exhibited a significant quantitative difference ($p<0.05$) in women without or with clinical diagnosis of pre-eclampsia.

Therefore, these microvesicle-encapsulated proteins could be used as biomarkers that will be diagnostic of pre-eclampsia.

Example 19

Differential Distribution of Proteins in AnnexinV-Versus CTB-Binding Microvesicles in Plasma of Pregnant Women (Third Trimester) without or with Clinical Diagnosis of Pre-Eclampsia—Combinations of Polypeptides The diagnostic power of these markers is greatly enhanced when they are used in combination of two proteins either in the same plasma microvesicle or different microvesicle (FIG. 10).

Using the logistic regression model (Moore et al, 2008), receiver operator characteristic (ROC) curves were constructed and the area under the curve for each marker in the CTB- or AV-bound microvesicles or a combination of two different markers were calculated (Table E1 and Table E2 below) For example, the area under the curve for PAI-1 and PLGF in the CTB-microvesicle were 0.972 and 0.833, respectively.

When PAI-1 and PLGF were combined, the area under the curve increased to 1.0 (Table E1 below).

TABLE E1

The receiver operator characteristic (ROC) curves were constructed for each of the biomarkers in the plasma CTB-microvesicles and the area under the curve for each marker or a combination of two different markers were calculated.

|  | Area under Curve |
|---|---|
| PAI-1 | .972 |
| PLGF | .833 |
| Procalcitonin | 1.000 |
| S-100b | .889 |
| TGF beta 2 | .972 |
| TIMP1 | .833 |
| PAI1 - PLGF | 1.000 |
| PAI1 - Procalcitonin | 1.000 |
| PAI1 - S100b | .972 |
| PAI1 - TGFbeta2 | 1.000 |
| PAI1 - TIMP1 | 1.000 |
| PLGF - Procalcitonin | 1.000 |
| PLGF - S100b | .889 |
| PLGF - TGFbeta2 | 1.000 |
| PLGF - TIMP1 | .917 |
| Procalcitonin - S100b | 1.000 |
| Procalcitonin - TGFbeta2 | 1.000 |
| Procalcitonin - TIMP1 | 1.000 |
| S100b - TGFbeta2 | 1.000 |
| S100b - TIMP1 | .917 |
| TGFbeta2 - TIMP1 | .972 |

Similarly, combining two or more markers in the AV-microvesicle e.g. PLGF and Procalcitonin also enhanced their respective area under curve from 0.889 and 0.861 respectively to 1.0 (Table E2 below).

TABLE E2

The receiver operator characteristic (ROC) curves were constructed for each of the biomarkers in the plasma AV-microvesicles and the area under the curve for each marker or a combination of two different markers were calculated.

|  | Area under Curve |
|---|---|
| PAI-1 | 1.000 |
| PLGF | .889 |
| Procalcitonin | .861 |
| S-100b | .972 |
| TGF beta 2 | .972 |
| TIMP1 | 1.000 |
| PAI1 - PLGF | 1.000 |
| PAI1 - Procalcitonin | 1.000 |
| PAI1 - S100b | 1.000 |
| PAI1 - TGFbeta2 | 1.000 |
| PAI1 - TIMP1 | 1.000 |
| PLGF - Procalcitonin | 1.000 |
| PLGF - S100b | 1.000 |
| PLGF - TGFbeta2 | 1.000 |
| PLGF - TIMP1 | 1.000 |
| Procalcitonin - S100b | 1.000 |
| Procalcitonin - TGFbeta2 | 1.000 |
| Procalcitonin - TIMP1 | 1.000 |
| S100b - TGFbeta2 | 1.000 |
| S100b - TIMP1 | 1.000 |
| TGFbeta2 - TIMP1 | 1.000 |

These examples illustrate the robustness of these biomarkers to diagnose pre-eclampsia when used in combination of two or more.

REFERENCES

Carmo, A., M. Pedro, et al. (2003). "Platelet-derived exosomes: a new vascular redox signaling pathway." *Critical Care* 7(Suppl 3): P117.

de Gassart, A., C. Geminard, et al. (2003). "Lipid raft-associated protein sorting in exosomes." *Blood* 102(13): 4336-4344.

Dwyer, J. D. and V. A. Bloomfield (1982). "Cholera toxin mediated agglutination of ganglioside Gm1 containing phospholipid vesicles and Gm1-coated polystyrene spheres." *Biochemistry* 21(13): 3231-3234.

Fadok, V. A. and G. Chimini (2001). "The phagocytosis of apoptotic cells." *Semin Immunol* 13(6): 365-372.

Giri, P. K., N. A. Kruh, et al. (2010). "Proteomic analysis identifies highly antigenic proteins in exosomes from *M. tuberculosis*-infected and culture filtrate protein-treated macrophages." *PROTEOMICS* 10(17): 3190-3202.

Hoffmann, P. R., A. M. deCathelineau, et al. (2001). "Phosphatidylserine (PS) induces PS receptor-mediated macropinocytosis and promotes clearance of apoptotic cells." *J Cell Biol* 155(4): 649-659.

Keller, S., A. K. Konig, et al. (2009). "Systemic presence and tumor-growth promoting effect of ovarian carcinoma released exosomes." *Cancer Lett* 278(1): 73-81.

Krahling, S., M. K. Callahan, et al. (1999). "Exposure of phosphatidylserine is a general feature in the phagocytosis of apoptotic lymphocytes by macrophages." *Cell Death Differ* 6(2): 183-189.

Laulagnier, K., C. Motta, et al. (2004). "Mast cell- and dendritic cell-derived exosomes display a specific lipid composition and an unusual membrane organization." *Biochem. J.* 380(1): 161-171.

Moore, R. G., et al., The use of multiple novel tumor biomarkers for the detection of ovarian carcinoma in patients with a pelvic mass. Gynecol Oncol, 2008. 108(2): p. 402-8.

Morelli, A. E., A. T. Larregina, et al. (2004). "Endocytosis, intracellular sorting, and processing of exosomes by dendritic cells." *Blood* 104(10): 3257-3266.

Rajendran, L., M. Honsho, et al. (2006). "Alzheimer's disease beta-amyloid peptides are released in association with exosomes." *Proc Natl Acad Sci USA* 103(30): 11172-11177.

Ratajczak, J., Wysoczynski, M., Hayek, F., Janowska-Wieczorek, A. & Ratajczak, M. Z. Membrane-derived microvesicles: important and underappreciated mediators of cell-to-cell communication. *Leukemia* 20, 1487-1495 (2006).

Smalheiser, N. R. (2007). "Exosomal transfer of proteins and RNAs at synapses in the nervous system." *Biol Direct* 2: 35.

Taylor, D. D. and C. Gercel-Taylor (2005). "Tumour-derived exosomes and their role in cancer-associated T-cell signalling defects." *Br J Cancer* 92(2): 305-311.

Thery, C., M. Ostrowski, et al. (2009). "Membrane vesicles as conveyors of immune responses." *Nat Rev Immunol* 9(8): 581-593.

Vance, J. E. (2008). "Thematic Review Series: Glycerolipids. Phosphatidylserine and phosphatidylethanolamine in mammalian cells: two metabolically related aminophospholipids." *Journal of Lipid Research* 49(7): 1377-1387.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of monitoring the state of a cell, tissue, organ or organism, and treating a cardiovascular disease state, the method comprising establishing, for a sample of microparticles from the cell, tissue, organ or organism, a ratio of:
    (i) (a) a selected polypeptide in microparticles which comprise GM1 gangliosides to
    (b) the selected polypeptide in microparticles which comprise exposed phosphotidylserine wherein the (a) to (b) ratio is indicative of the state of the cell, tissue, organ or organism
    (ii) wherein if the ratio of (a) to (b) is higher in the sample of microparticles relative to a control sample, administering a cardiovascular disease treatment to the cell, tissue, organ or organism.

2. The method of claim 1, further comprising a step of selecting microparticles by size or which comprises establishing a profile comprising a plurality of GM1 ganglioside microparticle polypeptide to Annexin V microparticle ratios for a plurality of selected polypeptide species.

3. The method of claim 1, wherein the cardiovascular disease state comprises a Chronic Heart Failure disease state or an Acute Myocardial Ischemia (AMI) state, or a pre-eclampsia state.

4. The method of claim 1, wherein the state of the cell, tissue, organ, or organism comprises a pre-eclampsia state and wherein the polypeptide comprises one or a combination of PAI-1, PLGF, Pro-calcitonin, S100b, TGFβ, or TIMP-1.

5. The method of claim 1, wherein
    (a) the microparticles comprise CD9+ microparticles;
    (b) the microparticles comprise microvesicles, exosomes, ectosomes or apoptotic bodies;
    (c) the state of the cell, tissue, organ or organism comprises a physiological state, a differentiation state, a development state or a metabolic state or a pathological state, a disease state, a human disease state, a food poisoning state, a diabetic state, an immune disorder state, a neurodegenerative disorder state, an oncogenic state, a cancerous state or a tumour state;
    (d) the state of the cell, tissue, organ or organism comprises a state of being sick, a state of poor prognosis, a state of recovery from sickness, a state of good prognosis or a healthy state;
    (e) the sample is selected from the group consisting of: urine, blood, tears, saliva, bronchoaveolar fluid, tumoral effusions, epididymal fluid, amniotic fluid and milk; or
    (f) any combination of the above.

6. The method of claim 1, which further comprises a step of normalising the level, concentration or amount of the selected polypeptide between two or more samples, in which the normalisation is conducted with reference to BNP, CD9 and/or TIMP-1 polypeptide.

7. The method of claim 1, wherein the microparticles which comprise GM1 gangliosides bind to Cholera Toxin B (CTB) and/or wherein the microparticles which comprise exposed phosphotidylserine bind to Annexin V.

8. The method of claim 1, wherein the selected polypeptide is CD9.

* * * * *